US010286427B2

(12) United States Patent
Vasquez et al.

(10) Patent No.: US 10,286,427 B2
(45) Date of Patent: May 14, 2019

(54) APPARATUS AND METHOD FOR CLEANING AN INSTRUMENT

(71) Applicant: STRYKER SUSTAINABILITY SOLUTIONS, INC., Tempe, AZ (US)

(72) Inventors: Jose Vasquez, Tampa, FL (US); Luis Diaz, Avon Park, FL (US); Dan Peterson, Lakeland, FL (US); Ed Cantey, Lakeland, FL (US); Jody Berkey, Lakeland, FL (US); Dan Fowler, Lakeland, FL (US); Brian Thomas, Auburndale, FL (US); Miguel J. Gonzalez, Lakeland, FL (US)

(73) Assignee: STRYKER SUSTAINABILITY SOLUTIONS, INC., Tempe, AZ (US)

( * ) Notice: Subject to any disclaimer, the term of this patent is extended or adjusted under 35 U.S.C. 154(b) by 0 days.

(21) Appl. No.: 16/008,397

(22) Filed: Jun. 14, 2018

(65) Prior Publication Data

US 2018/0289446 A1 Oct. 11, 2018

Related U.S. Application Data

(62) Division of application No. 14/572,573, filed on Dec. 16, 2014, now Pat. No. 10,022,189.

(Continued)

(51) Int. Cl.
*A61L 2/00* (2006.01)
*B08B 9/00* (2006.01)
(Continued)

(52) U.S. Cl.
CPC ............ *B08B 9/00* (2013.01); *A61B 90/70* (2016.02); *B08B 3/12* (2013.01); *B08B 11/02* (2013.01); *A61L 2/025* (2013.01); *A61L 2202/17* (2013.01)

(58) Field of Classification Search
None
See application file for complete search history.

(56) References Cited

U.S. PATENT DOCUMENTS

| 1,540,793 A | 6/1925 | Maloney |
| 3,807,954 A | 4/1974 | McDonald |
| (Continued) | | |

FOREIGN PATENT DOCUMENTS

| DE | 3416743 A1 | 7/1985 |
| DE | 19858344 A1 | 6/1999 |
| (Continued) | | |

OTHER PUBLICATIONS

American Machinist, Tips on ultrasonic cleaning, Feb. 12, 2009, American Machinist, 8 paragraphs.

(Continued)

*Primary Examiner* — Mikhail Kornakov
*Assistant Examiner* — Ryan L. Coleman
(74) *Attorney, Agent, or Firm* — Howard & Howard Attorneys PLLC

(57) ABSTRACT

An apparatus for cleaning an instrument with a cleaning fluid includes a vessel defining a chamber and a port for at least partially filling the chamber with the fluid. The apparatus further includes an ultrasonic transducer for delivering ultrasonic energy to the fluid, and a vacuum pump for depressurizing the chamber. The apparatus further includes a rotatable device removably disposable in the chamber and having a rack defining a cavity for supporting the instrument. The rotatable device also has a fluid delivery member extending toward the cavity and having a fluid channel between an inlet and an outlet. The apparatus further includes a fluid transmission system in fluid communication with the chamber and the fluid channel of the fluid delivery member for circulating the fluid from the chamber through (Continued)

the fluid channel of the fluid delivery member. A method of cleaning an instrument is also provided.

19 Claims, 8 Drawing Sheets

Related U.S. Application Data

(60) Provisional application No. 61/916,477, filed on Dec. 16, 2013.

(51) Int. Cl.
- *B08B 3/12* (2006.01)
- *B08B 11/02* (2006.01)
- *A61B 90/70* (2016.01)
- *A61L 2/025* (2006.01)

(56) References Cited

U.S. PATENT DOCUMENTS

| | | |
|---|---|---|
| 3,814,901 A | 6/1974 | Morhack |
| 3,893,843 A | 7/1975 | Fry et al. |
| 4,064,886 A | 12/1977 | Heckele |
| 4,142,539 A | 3/1979 | Shih et al. |
| 4,193,818 A | 3/1980 | Young et al. |
| 4,203,943 A | 5/1980 | Gills et al. |
| 4,239,730 A | 12/1980 | Fahlvik et al. |
| 4,261,950 A | 4/1981 | Bainbridge et al. |
| 4,278,101 A | 7/1981 | Tanaka et al. |
| 4,281,674 A | 8/1981 | Tanaka et al. |
| 4,321,232 A | 3/1982 | Bithell |
| 4,333,773 A | 6/1982 | Fjalstrom |
| 4,337,223 A | 6/1982 | Kaye |
| 4,380,530 A | 4/1983 | Kaye |
| 4,410,492 A | 10/1983 | Kaye |
| 4,489,741 A | 12/1984 | Ogasawara |
| 4,526,622 A | 7/1985 | Takamura et al. |
| 4,526,623 A | 7/1985 | Ishii et al. |
| 4,537,209 A | 8/1985 | Sasa |
| 4,545,956 A | 10/1985 | Ciszewski et al. |
| 4,548,197 A | 10/1985 | Kinoshita |
| 4,552,728 A | 11/1985 | Taylor |
| 4,576,650 A | 3/1986 | Yabe et al. |
| 4,576,792 A | 3/1986 | Martensson |
| 4,579,597 A | 4/1986 | Sasa et al. |
| 4,579,598 A | 4/1986 | Sasa et al. |
| 4,590,037 A | 5/1986 | Kaye |
| 4,637,916 A | 1/1987 | Henebert et al. |
| 4,643,876 A | 2/1987 | Jacobs et al. |
| 4,710,233 A | 12/1987 | Hohmann et al. |
| 4,731,222 A | 3/1988 | Kralovic et al. |
| 4,744,951 A | 5/1988 | Cummings et al. |
| 4,756,882 A | 7/1988 | Jacobs et al. |
| 4,765,963 A | 8/1988 | Mukogawa et al. |
| 4,784,790 A | 11/1988 | Disch et al. |
| 4,862,872 A | 9/1989 | Yabe et al. |
| 4,863,688 A | 9/1989 | Schmidt et al. |
| 4,892,706 A | 1/1990 | Kralovic et al. |
| 4,908,188 A | 3/1990 | Jefferies, III et al. |
| 4,911,190 A | 3/1990 | Sheldon |
| 4,928,917 A | 5/1990 | Wolf |
| 4,937,046 A | 6/1990 | Anderson et al. |
| 4,943,414 A | 7/1990 | Jacobs et al. |
| 4,952,370 A | 8/1990 | Cummings et al. |
| 4,956,145 A | 9/1990 | Cummings et al. |
| 5,017,241 A | 5/1991 | Ryan |
| 5,027,840 A | 7/1991 | Nezworski |
| 5,035,752 A | 7/1991 | Tanaka et al. |
| 5,037,623 A | 8/1991 | Schneider et al. |
| 5,077,008 A | 12/1991 | Kralovic et al. |
| 5,090,433 A | 2/1992 | Kamaga |
| 5,091,343 A | 2/1992 | Schneider et al. |
| 5,091,345 A | 2/1992 | Becker |
| 5,114,596 A | 5/1992 | Laterra |
| 5,116,575 A | 5/1992 | Badertscher et al. |
| 5,118,471 A | 6/1992 | Anderson et al. |
| 5,120,512 A | 6/1992 | Masuda |
| 5,122,344 A | 6/1992 | Schmoegner |
| 5,125,981 A | 6/1992 | Belanger et al. |
| 5,132,084 A | 7/1992 | Harrell et al. |
| 5,145,641 A | 9/1992 | Shelley |
| 5,176,884 A | 1/1993 | Taschner et al. |
| 5,186,893 A | 2/1993 | Moulton et al. |
| 5,190,666 A | 3/1993 | Bisconte |
| 5,209,909 A | 5/1993 | Siegel et al. |
| 5,217,698 A | 6/1993 | Siegel et al. |
| 5,225,160 A | 7/1993 | Sanford et al. |
| 5,227,132 A | 7/1993 | Anderson et al. |
| 5,260,021 A | 11/1993 | Zeleznick |
| 5,266,275 A | 11/1993 | Faddis |
| 5,279,799 A | 1/1994 | Moser |
| 5,281,401 A | 1/1994 | Bryson, Sr. |
| 5,288,467 A | 2/1994 | Biermaier |
| 5,310,524 A | 5/1994 | Campbell et al. |
| 5,348,711 A | 9/1994 | Johnson et al. |
| 5,350,563 A | 9/1994 | Kralovic et al. |
| 5,364,602 A | 11/1994 | Leduc |
| 5,374,394 A | 12/1994 | Kralovic |
| 5,391,360 A | 2/1995 | Kochte et al. |
| 5,395,240 A | 3/1995 | Paschke et al. |
| 5,405,587 A | 4/1995 | Fernandez et al. |
| 5,407,648 A | 4/1995 | Allen et al. |
| 5,407,685 A | 4/1995 | Malchesky et al. |
| 5,425,815 A | 6/1995 | Parker et al. |
| 5,439,654 A | 8/1995 | Kochte |
| 5,441,707 A | 8/1995 | Lewis et al. |
| 5,443,801 A | 8/1995 | Langford |
| 5,445,792 A | 8/1995 | Rickloff et al. |
| 5,492,671 A | 2/1996 | Krafft |
| 5,492,672 A | 2/1996 | Childers et al. |
| 5,494,530 A | 2/1996 | Graf |
| 5,494,637 A | 2/1996 | Barlow |
| 5,505,218 A | 4/1996 | Steinhauser |
| 5,508,009 A | 4/1996 | Rickloff et al. |
| 5,527,508 A | 6/1996 | Childers et al. |
| 5,529,750 A | 6/1996 | Kochte |
| 5,533,539 A | 7/1996 | Sutter et al. |
| 5,534,221 A | 7/1996 | Hillebrenner et al. |
| 5,540,901 A | 7/1996 | Riley |
| 5,547,456 A | 8/1996 | Strobl et al. |
| 5,552,115 A | 9/1996 | Malchesky |
| 5,556,607 A | 9/1996 | Childers et al. |
| 5,558,841 A | 9/1996 | Nakagawa et al. |
| 5,571,488 A | 11/1996 | Beerstecher et al. |
| 5,580,530 A | 12/1996 | Kowatsch et al. |
| 5,589,507 A | 12/1996 | Hall, II et al. |
| 5,609,821 A | 3/1997 | Grimberg et al. |
| 5,628,971 A | 5/1997 | Norman |
| 5,662,866 A | 9/1997 | Siegel et al. |
| 5,686,045 A | 11/1997 | Carter |
| 5,711,921 A | 1/1998 | Langford |
| 5,723,090 A | 3/1998 | Beerstecher et al. |
| 5,732,614 A | 3/1998 | Oslin |
| 5,753,195 A | 5/1998 | Langford et al. |
| 5,759,490 A | 6/1998 | Malchesky |
| 5,792,422 A | 8/1998 | Lin et al. |
| 5,795,403 A | 8/1998 | Biermaier |
| 5,804,139 A | 9/1998 | Lin et al. |
| 5,833,935 A | 11/1998 | Malchesky |
| 5,840,251 A | 11/1998 | Iwaki |
| 5,851,485 A | 12/1998 | Lin et al. |
| 5,858,305 A | 1/1999 | Malchesky |
| 5,868,667 A | 2/1999 | Lin et al. |
| 5,871,692 A | 2/1999 | Haire et al. |
| 5,876,501 A | 3/1999 | Bajkowski |
| 5,876,507 A | 3/1999 | Bajkowski |
| 5,882,589 A | 3/1999 | Mariotti |
| 5,902,413 A | 5/1999 | Puzsko et al. |
| 5,906,802 A | 5/1999 | Langford |
| 5,921,256 A | 7/1999 | Barin |
| 5,923,432 A | 7/1999 | Kral |
| 5,937,875 A | 8/1999 | Nygren |
| 5,958,038 A | 9/1999 | Agrawal et al. |

(56) References Cited

U.S. PATENT DOCUMENTS

| | | |
|---|---|---|
| 5,961,921 A | 10/1999 | Addy et al. |
| 5,961,922 A | 10/1999 | Witte et al. |
| 5,980,825 A | 11/1999 | Addy et al. |
| 5,985,038 A | 11/1999 | Dawson |
| 6,001,305 A | 12/1999 | Mueller |
| 6,013,227 A | 1/2000 | Lin et al. |
| 6,015,529 A | 1/2000 | Lin et al. |
| 6,027,572 A | 2/2000 | Labib et al. |
| 6,036,928 A | 3/2000 | Barnstead |
| 6,041,794 A | 3/2000 | Lin et al. |
| 6,047,431 A | 4/2000 | Canonica |
| 6,066,294 A | 5/2000 | Lin et al. |
| 6,068,815 A | 5/2000 | Oberleitner et al. |
| 6,068,825 A | 5/2000 | Tsunematsu |
| 6,083,458 A | 7/2000 | Licha et al. |
| 6,083,485 A | 7/2000 | Licha et al. |
| 6,158,450 A | 12/2000 | Painter |
| 6,162,395 A | 12/2000 | Kowanko |
| 6,187,266 B1 | 2/2001 | Lin et al. |
| 6,203,756 B1 | 3/2001 | Lin et al. |
| 6,224,828 B1 | 5/2001 | Lin |
| 6,257,254 B1 | 7/2001 | Rochette et al. |
| 6,286,527 B1 | 9/2001 | Stanley |
| 6,379,632 B1 | 4/2002 | Kinoshita et al. |
| 6,423,266 B1 | 7/2002 | Choperena |
| 6,431,187 B1 | 8/2002 | Painter |
| 6,439,248 B2 | 8/2002 | Rochette et al. |
| 6,528,015 B1 | 3/2003 | Lin |
| 6,538,360 B2 | 3/2003 | Puskas |
| 6,558,620 B1 | 5/2003 | Sanford et al. |
| 6,568,409 B1 | 5/2003 | Fleck |
| 6,582,654 B1 | 6/2003 | Kral et al. |
| 6,585,943 B1 | 7/2003 | Sanford et al. |
| 6,596,232 B1 | 7/2003 | Lin et al. |
| 6,608,815 B1 | 8/2003 | Huang et al. |
| 6,645,430 B1 | 11/2003 | Lin |
| 6,656,427 B2 | 12/2003 | Lin et al. |
| 6,685,895 B1 | 2/2004 | Lin et al. |
| 6,797,245 B2 | 9/2004 | Nakanishi et al. |
| 6,814,932 B2 | 11/2004 | Hlebovy et al. |
| 6,884,392 B2 | 4/2005 | Malkin et al. |
| 7,128,075 B2 | 10/2006 | Publ |
| 7,138,087 B1 | 11/2006 | Malkin et al. |
| 7,353,832 B2 | 4/2008 | Stockert et al. |
| 7,608,218 B2 | 10/2009 | Fry et al. |
| 7,625,534 B2 | 12/2009 | Horacek et al. |
| 7,841,104 B2 | 11/2010 | Robert et al. |
| 7,910,072 B2 | 3/2011 | Jethrow |
| 8,012,425 B2 | 9/2011 | Horacek et al. |
| 10,022,189 B2 | 7/2018 | Vasquez et al. |
| 2008/0286178 A1 | 11/2008 | Yardimci et al. |
| 2010/0192978 A1 | 8/2010 | Plavidal et al. |
| 2011/0132404 A1* | 6/2011 | Lutz .................... A61L 2/025 |
| | | 134/19 |

FOREIGN PATENT DOCUMENTS

| | | |
|---|---|---|
| DE | 19858347 A1 | 6/1999 |
| EP | 0302419 A2 | 2/1989 |
| EP | 0766969 A1 | 4/1997 |
| EP | 0835665 A2 | 4/1998 |
| EP | 0898971 A2 | 3/1999 |
| EP | 0923951 A2 | 6/1999 |
| EP | 1186307 A2 | 3/2002 |
| EP | 1192954 A2 | 4/2002 |
| GB | 2094149 A | 9/1982 |
| GB | 2248188 A | 4/1992 |
| WO | 9522353 A1 | 8/1995 |
| WO | 9724147 A1 | 7/1997 |
| WO | 0018521 A1 | 4/2000 |
| WO | 0023118 A1 | 4/2000 |

OTHER PUBLICATIONS

English language abstract and translation for DE3416743 extracted from espacenet.com database on Apr. 21, 2015, 41 pages.

English language abstract and translation for WO9522353 extracted from espacenet.com database on Apr. 21, 2015, 23 pages.

English language abstract for DE19858344 extracted from espacenet.com database on Apr. 21, 2015, 35 pages. Also see English language equivalent U.S. Pat. No. 6,645,430.

English language abstract for DE19858347 extracted from espacenet.com database on Apr. 21, 2015, 35 pages. Also see English language equivalent U.S. Pat. No. 6,494,964.

Proceco, Dring after Aqueous Parts Cleaning, Apr. 1, 2002, Proceco, date stamp, tittle, 5 paragraphs.

W AN Assenburg & Co b.v.; Technical Documentation; Cleaning- and disinfection system for endoscopes; machine type/Wasseenburg EDS 03; Applin/GE; Machine No. 005—(1997).

* cited by examiner

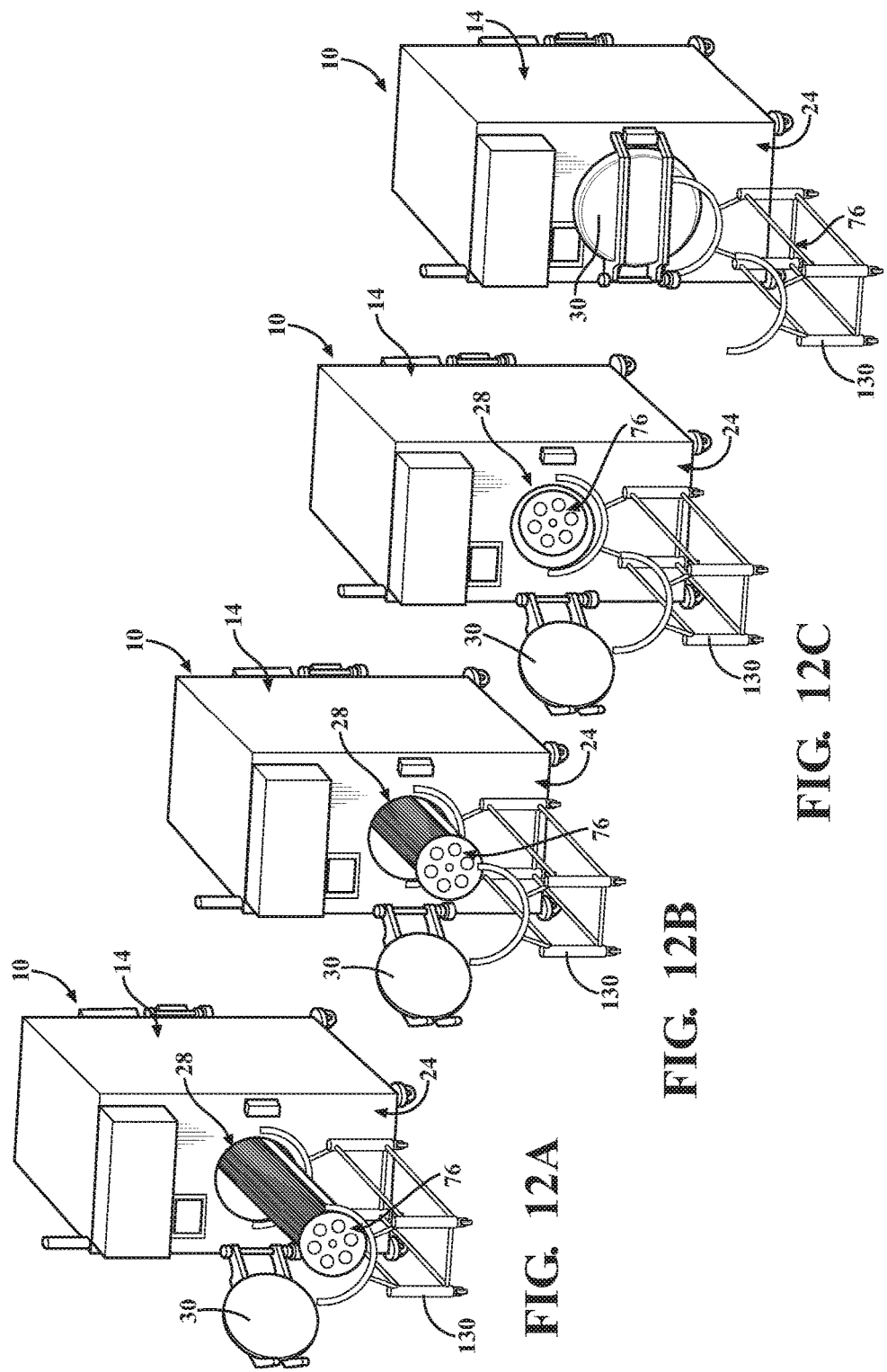

APPARATUS AND METHOD FOR CLEANING AN INSTRUMENT

CROSS REFERENCE TO RELATED APPLICATIONS

This application is a divisional of U.S. patent application Ser. No. 14/572,573 filed on Dec. 16, 2014, which claims priority to and all the benefits of U.S. Provisional Patent Application No. 61/916,477 filed on Dec. 16, 2013. The contents of U.S. patent application Ser. No. 14/572,573 and U.S. Provisional Patent Application No. 61/916,477 are expressly incorporated herein by reference in their entirety.

FIELD OF THE INVENTION

The present disclosure relates generally to an apparatus and method for cleaning an instrument.

BACKGROUND

Medical instruments, including those which are classified as endoscopic and non-endoscopic, often get coated with biological fluid, such as blood, when used during a medical procedure. In some cases, these medical instruments can be reused after they have been properly cleaned, reconditioned, sterilized, and/or decontaminated. Current cleaning apparatuses typically subject the instruments to a high temperature and/or a cleaning fluid(s). However, in some instances, the biological fluid(s) may harden or dry before cleaning. Accordingly, the biological fluid(s) may undesirably remain on interior and/or exterior surfaces of the instruments after cleaning. Additionally, the inventors of the subject application discovered that some cleaning apparatuses do not allow the cleaning fluid(s) to adequately contact the interior of the instrument. Accordingly, it may be difficult to effectively remove the biological fluid that is deposited within the instrument. For at least these reasons, there is an opportunity to develop an improved apparatus and method for cleaning instruments, such as medical instruments.

SUMMARY

An apparatus for cleaning an instrument with a cleaning fluid comprises a vessel defining a chamber and a port for at least partially filling the chamber with the cleaning fluid. The apparatus further comprises an ultrasonic transducer operatively coupled to the vessel for delivering ultrasonic energy to the cleaning fluid that is disposed within the chamber. The apparatus further comprises a vacuum pump operatively coupled to the vessel for depressurizing the chamber. The apparatus further comprises a rotatable device removably disposable in the chamber and defining a longitudinal axis. The rotatable device has a rack defining a cavity for supporting the instrument. The rotatable device further has a fluid delivery member extending towards the cavity of the rack. The fluid delivery member has an inlet and an outlet, and the fluid delivery member defines a fluid channel extending between the inlet and the outlet. The apparatus further comprises a fluid transmission system in fluid communication with the chamber and the fluid channel of the fluid delivery member for circulating the cleaning fluid from the chamber through the fluid channel of the fluid delivery member.

A method for cleaning an instrument is also provided. The method comprises loading the instrument in the cavity of the rack, placing the rotatable device inside the chamber of the vessel, at least partially filling the chamber with the cleaning fluid to submerge the instrument in the cleaning fluid, sonicating the cleaning fluid in the chamber with the ultrasonic transducer, and circulating the cleaning fluid through the fluid channel in the fluid delivery member such that the cleaning fluid exits the fluid delivery member to contact the interior of the instrument.

BRIEF DESCRIPTION OF THE DRAWINGS

Advantages of the present disclosure will be readily appreciated, as the same becomes better understood by reference to the following detailed description, when considered in connection with the accompanying drawings. It is to be appreciated that the figures are merely illustrative and are not necessarily drawn to scale.

FIGS. 12A through 12D are perspective views of the cleaning apparatus illustrating the loading of the rotatable device in the chamber of the vessel.

DETAILED DESCRIPTION

Figure 1:
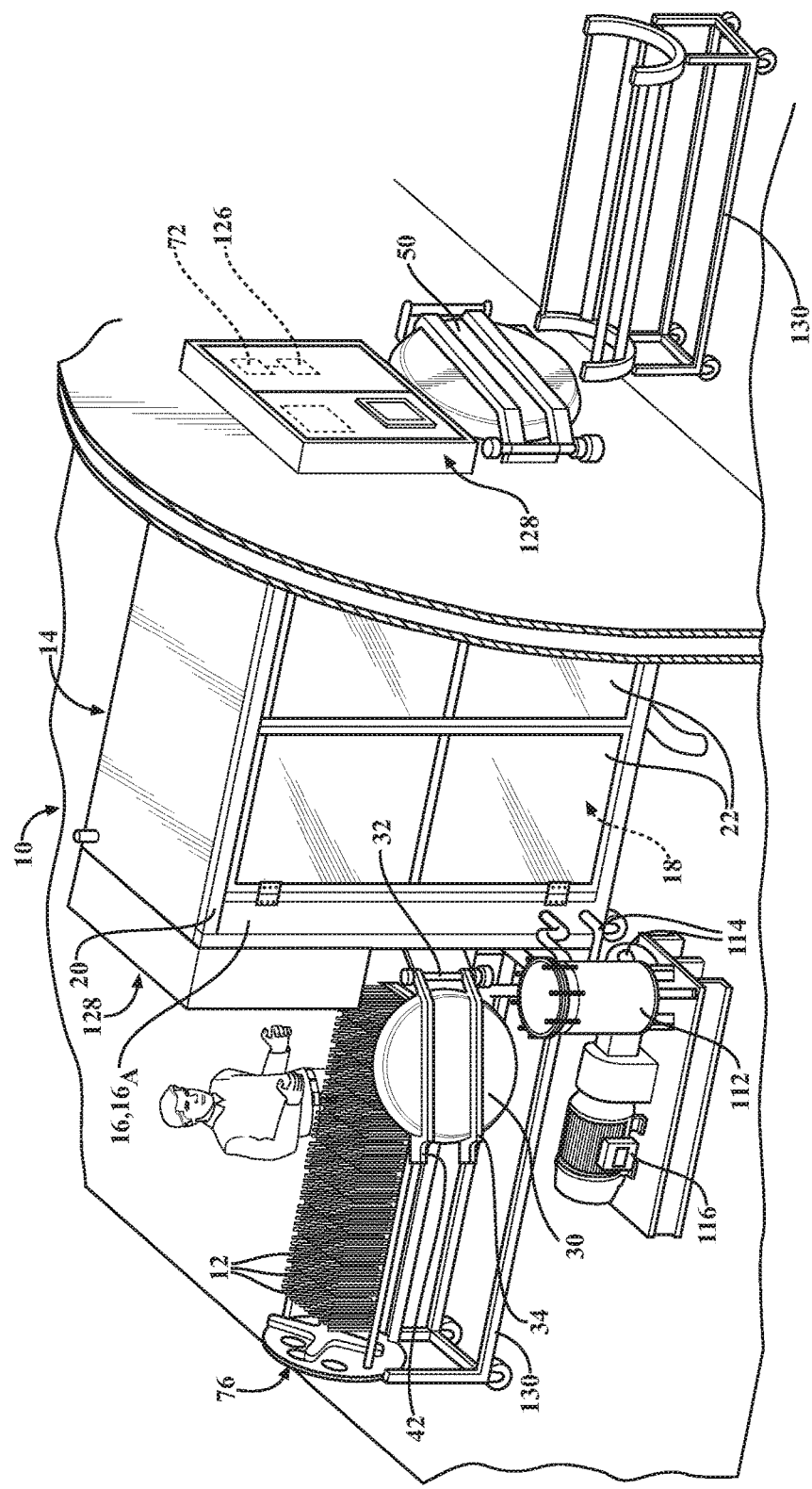
FIG. 1 is a semi-schematic, perspective view of an embodiment of the cleaning apparatus.

Referring now to the figures, wherein like numerals indicate corresponding parts throughout the several views, an apparatus 10 for cleaning an instrument 12 is shown throughout FIGS. 1-5, 5A, 6-11, and 12A-12D and is described in detail below. The apparatus 10 may be used to effectively and efficiently clean the interior and/or exterior of the instrument 12 with a cleaning fluid. In an example, the apparatus 10 may be used to clean a single (i.e., one) instrument 12. In another example, the apparatus 10 may be used to clean a plurality of (i.e. two or more) instruments at the same time.

The instrument 12 may be any type of article or device that requires cleaning. In an example, the instrument 12 is a medical instrument, such as an endoscopic instrument or a non-endoscopic instrument. The instrument 12 typically has an interior and an exterior. In some instances, however, the instrument 12 may have an exterior, but not an interior. Non-limiting examples of the instrument 12 include trocars (such as ENDOPATH® XCEL® trocars and ENDOPATH®

BASX™ trocars available from Ethicon Endo-Surgery, Inc.), laparoscopic hand instruments (such as ENSEAL® G2 curved and straight tissue sealers available from Ethicon Endo-Surgery, Inc. and ENDO DISSECT™, Short and ENDO SHEARS™ Short instruments available from Coviden Surgical), suture passers, reamers, drill bits, saws, precision blades, oscillating blades, arthroscopic instruments (such as DYONICS™ arthroscopic drill bits and saw blades available from Smith & Nephew, arthroscopic instruments available from Linvatec Corporation, and arthroscopic instruments available from Stryker Corporation), and/or the like.

It is to be understood that the instrument 12 may also be an instrument other than a medical instrument. Non-limiting examples of other instruments include cooking instruments (such as knives, forks, spoons, measuring instruments, etc.), household instruments, laboratory instruments (such as test tubes, beakers, thermometers, etc.), veterinary instruments, and/or the like.

In certain embodiments, the interior of the instrument 12 may be understood to include at least one surface defining a lumen of the instrument 12. In other embodiments, the interior of the instrument 12 may be understood as a surface that is not readily visible while the instrument 12 is intact (i.e., not disassembled).

In certain embodiments, the instrument 12 may be a used medical device that is received from one or more hospitals. Once the used medical devices arrive at the facility, depending on the condition of the used medical device, the used medical device may be also reconditioned. The step of reconditioning may include sharpening edges, removing burrs, and/or rebuilding the used medical device. The reconditioned medical device may be tested using one or more of the following testing systems: electrical profiling, examining high-speed rotation, measuring curvature, evaluating pressure decay, or other device-specific functional tests.

The apparatus 10 may be used to clean the instrument 12. Cleaning of the instrument 12 may include removing a substance (e.g., dirt, debris, particles of hardened biological fluid, the biological fluids themselves, stains, etc.) from the interior and/or exterior of the instrument 12. In certain embodiments, cleaning describe a process for disinfecting, sterilizing, and/or decontaminating the interior and/or exterior of the instrument 12.

The cleaning fluid may be any type of cleaning fluid that will suitably clean the instrument 12. Examples of suitable cleaning fluids include chemical-based cleaning fluids and/or natural cleaning fluids. Examples of specific cleaning fluids that may be used include enzymatic and/or peroxide-based cleaning fluids, water, detergents, and/or combinations thereof.

An embodiment of the apparatus 10 is shown in FIG. 1. In this embodiment, the apparatus 10 is capable of cleaning several (e.g., tens or hundreds) of instruments 12 at the same time. The apparatus 10 as shown may be used in large-scale environments and/or for commercial purposes where a high quantity (e.g., tens or hundreds) of instruments 12 are used, such as in hospitals, medical laboratories, schools, and/or the like. In large-scale environments, the apparatus 10 may be configured to operate in a single room, such as in a laboratory or cleaning room of a hospital. Alternatively, and as shown in the example depicted in FIG. 1, the apparatus 10 may be configured to be operated between two rooms, where the instrument(s) 12 is/are loaded into the apparatus 10 in a first room and the cleaned instrument(s) 12 is/are unloaded in a second room. It is to be understood, however, that the apparatus 10 may be designed to be larger or smaller depending, at least in part, on the intended end use of the apparatus 10. For example, the apparatus 10 may be designed for small-scale environments, where small quantities (e.g., between one and ten) instruments 12 are used such as in small medical offices or for home use. Typically, for small-scale environments, the apparatus 10 may be compact and usably typically in a one room.

As shown, the apparatus 10 comprises a housing 14. The housing defines an interior 18. As shown, the housing 14 may include a plurality of walls 16 such as a first side wall $16_A$, a second side wall $16_B$, a front wall $16_C$, and a rear wall $16_D$. While the housing 14 shown in the figures has four walls $16_A$, $16_B$, $16_C$, $16_D$, it is to be appreciated that the housing 12 may have fewer than or more than four walls 16 and may have shapes other than rectangular or cylindrical shapes. For example, the housing 14 may have one wall 16, two walls 16, three walls 16, five walls 16, etc.

In an embodiment, and as shown, the housing 14 may further include a frame 20 that supports the various walls 16. One or more of the side walls $16_A$ and $16_B$ may contain at least one door 22 to allow a user to access to the interior 18 of the housing 12, e.g., for purposes of maintenance and/or cleaning. The door 22 may be hinged or may slide in a conventional manner. In another embodiment, one or more of the side walls $16_A$ and $16_B$ are panels that are at least partially removable from the frame 20 to allow the user to access the interior 18 of the housing 12. In this embodiment, the respective top and bottom portions of the side walls $16_A$, $16_B$ are positioned into top and bottom tracks defined by the frame 20. The side walls $16_A$, $16_B$ can be removed, for example, by moving (such as sliding) the side walls $16_A$, $16_B$ along or in the tracks. In yet another embodiment, the side walls $16_A$, $16_B$ are integrally formed to frame 20 and are not removable from the frame 20.

The housing 14 may further include front 24 and rear 26 ends. As shown, the front wall $16_C$ is coupled to the frame 20, and is positioned at the front end 24 of the housing 14. The front wall $16_C$ includes an opening 28 defined in the front wall $16_C$ that provides access to the interior 18 of the housing 14. As will be described in further detail below, the opening 28 may be used as a loading venue for a rotatable device 76.

The housing 14 may further include a front door 30 which is coupled (such as mechanically coupled with fasteners or hinged) to the front wall $16_C$. The front door 30 may be described as a hatch or portal which may be opened to allow access to the interior 18 of the housing 14. For example, the front door 30 moves between open and closed positions relative to the opening 28. When in the open position, the front door 30 provides access to the opening 28 and to the interior 18 of the housing 14. It is to be understood that the front door 30 is considered to be in the opened position when the front door 30 exposes at least a portion of the opening 28 defined in the front wall $16_C$. When in the closed position, the front door 30 completely closes off the opening 28 and access to the interior 18 of the housing 14 cannot be obtained through the opening 28.

In an example, the housing 14 further includes a hinge 32 for coupling the front door 30 to the front wall $16_C$ and for enabling the front door 30 to move between the open and closed positions. The hinge 32 is typically mechanically coupled to the front wall $16_C$, such as with one or more fasteners. The hinge 32 is also typically mechanically coupled to the front door 30, such as with one or more fasteners.

As shown, the front door 30 includes a handle 34 which may be held, gripped, and/or grasped by, for example, a user of the apparatus 10 for opening and closing the front door 30. The handle 34 may be a bar, a rod, a plate, a knob, and/or the like. In an example, the handle 34 is a bar or a rod that extends at least partially across a width $W_{FD}$ of the front door 30. As shown, the handle 34 extends across and beyond the width $W_{FD}$ of the front door 30. Further, the handle 34 may be coupled to the front door 30. Alternatively, and as shown, the handle may be coupled to the hinge 32. In this example, the handle 34 has two ends 36, 38, and the handle 34 is coupled to the hinge 32 at one of the ends 36, 38. As shown, the handle 34 is coupled to the hinge 32 at the end 36.

The housing 14 may further include a locking mechanism 40 for locking the front door 30 when in the closed position. In an example, the locking mechanism 40 includes a first locking member 42 coupled to the front door 30 and a second locking member 44 coupled to the front wall $16_C$. The second locking member 44 is complementary to and configured to mate with the first locking member 42. In another example, the first locking member 42 may be coupled to the handle 34 and the second locking member 44 may be coupled to the front wall $16_C$. The first locking member 42 may be coupled to one of the ends 36, 38 of the handle 34. As shown, the first locking member 42 is coupled to the end 38 while the hinge 32 is coupled to the other end 36. In an example, the locking mechanism 40 may include one or more pneumatic rotating locking cylinders (not shown) coupled to the housing 14 for latching the front door 30 to the housing 14 when the front door 30 is in the closed position.

Figure 4:
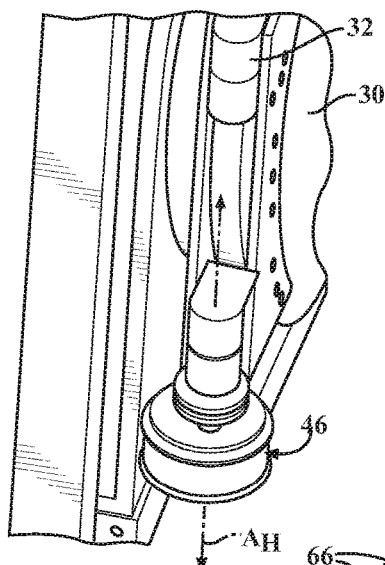
FIG. 4 is a perspective view of a portion of the housing of the cleaning apparatus showing a motor for opening and closing a front door.

In an example, and as shown, e.g., in FIG. 4, the hinge 32 is coupled to the housing 14 and has a hinge axis $A_H$. The apparatus 10 may further include a motor 46 (such as a rotating or electric motor) that is operatively coupled to the front door 30. In an example, the motor 46 operates to move the front door 30 between the open and closed positions. In an example, the motor 46 may operate the front door 30 directly. In another example, the motor 46 may operate the front door 30 utilizing a timing belt system (not shown). For instance, the front door 30 may have an axle (not shown), and the timing belt system causes the axle of the front door 30 to rotate or spin about the hinge axis $A_H$. Where the motor 46 is present, a handle 34 is not required for the front door 30.

Figure 2:
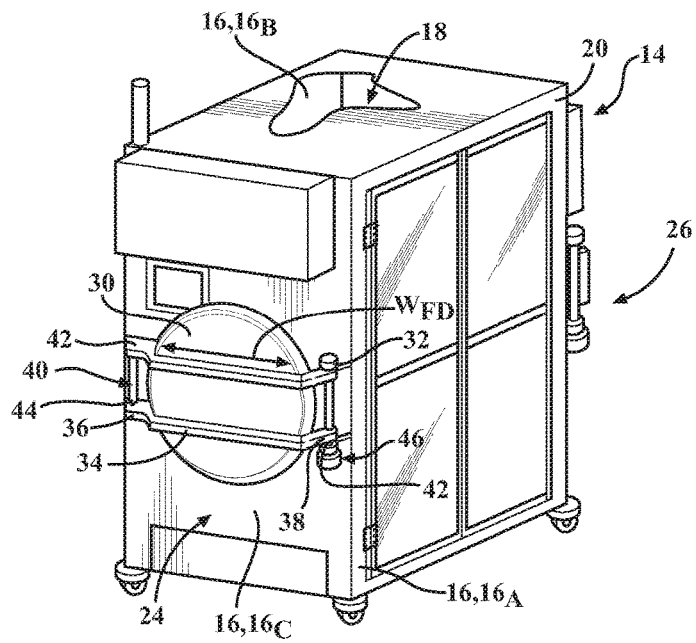
FIG. 2 is a perspective view of a housing of the cleaning apparatus.
Figure 3:
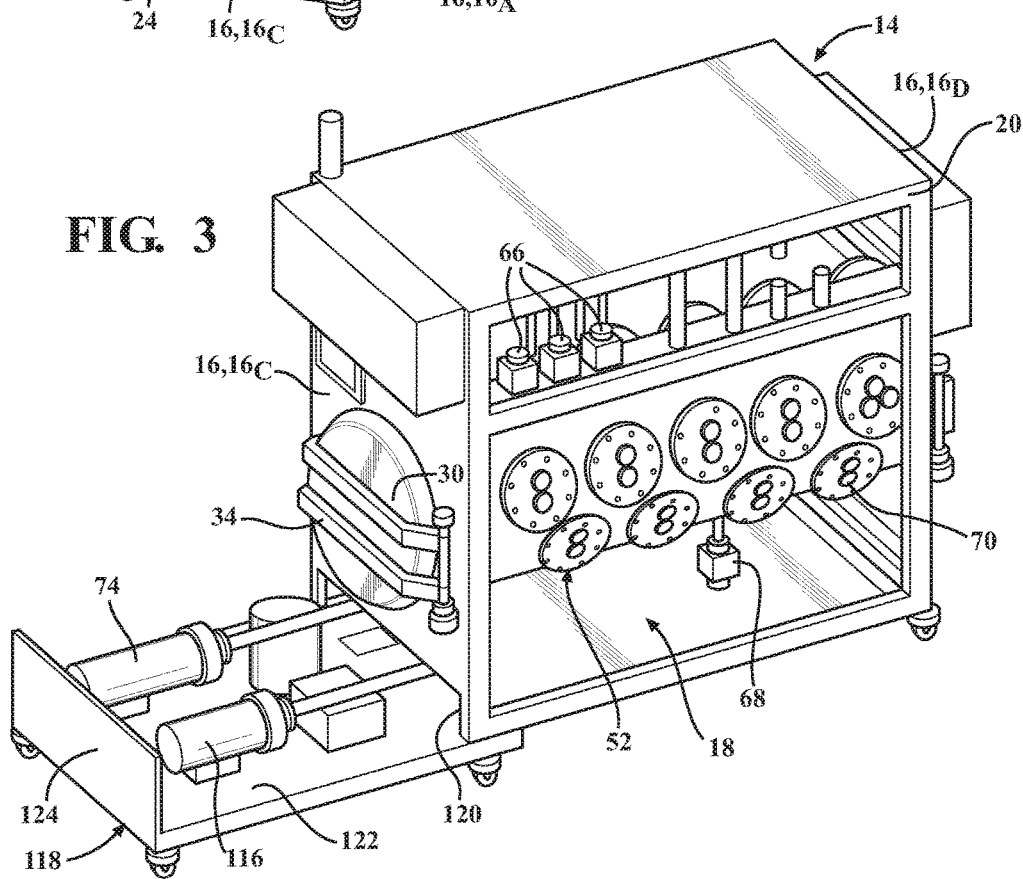
FIG. 3 is a perspective view of the housing of FIG. 2 with the side walls removed.

As shown, e.g., in FIGS. 1-3, the rear wall $16_D$ is coupled to the frame 20, and is positioned at the rear end 26 of the housing 14. The rear wall $16_D$ includes another opening (not shown) defined in the rear wall $16_D$ that also provides access to the interior 18 of the housing 14. As will be described in further detail below, the other opening may be used as an unloading venue for the rotatable device 76.

The housing 14 further includes a rear door 50 which is coupled (such as mechanically coupled) to the rear wall $16_D$. The rear door 50 may be described as a hatch or portal which may be opened for access to the interior 18 of the housing 14. For example, the rear door moves between open and closed positions relative to the other opening. When in the open position, the rear door 50 provides access to the other opening and to the interior 18 of the housing 14. It is to be understood that the rear door 50 is considered to be in the opened position when the rear door 50 exposes at least a portion of the opening other opening defined in the rear wall $16_D$. When in the closed position, the rear door 50 may completely close off the other opening and access to the interior 18 of the housing 14 cannot be obtained through the other opening.

The rear door 50 may have a similar or different design as the front door 30. In one example, the rear door 50 is a mirror image or a 180° rotated copy of the front door 30, and operates in the same manner as the front door 30. However, the timing of the opening and closing the rear door 50 may be independent of the timing of opening and closing the front door 30. For instance, the front door 30 may be in the open position and the rear door 50 may be in the closed position when loading the rotatable device 76. Further, the front door 30 is in the closed position and the rear door 50 is in the open position when unloading the rotatable device 76.

Figure 5:
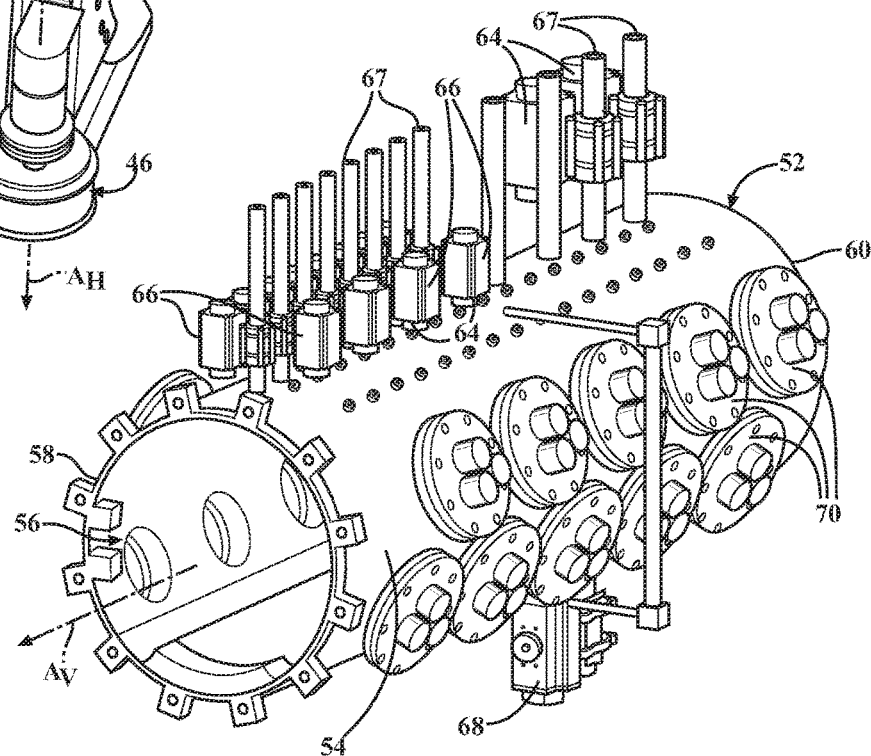
FIG. 5 is a perspective view of a vessel of the cleaning apparatus in accordance with one embodiment.
Figure 5A:
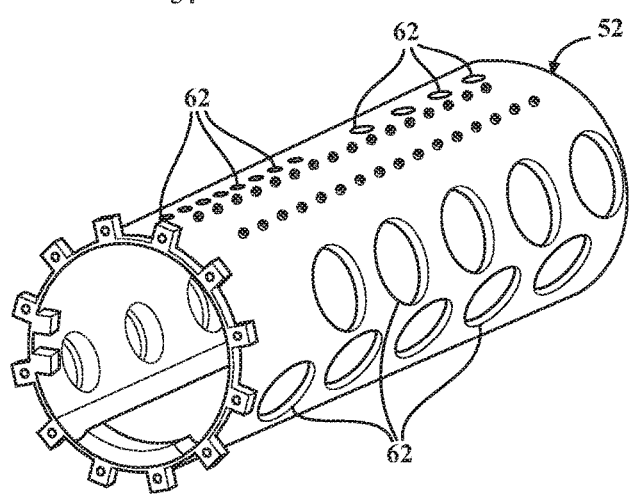
FIG. 5A is a perspective view of the vessel of FIG. 5 without the injectors, valves, and ultrasonic transducers.
Figure 6:
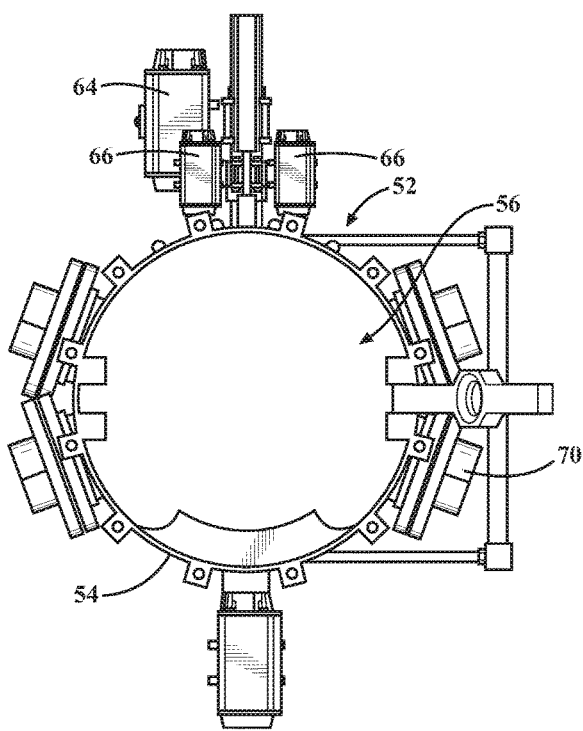
FIG. 6 is an end view of the vessel shown in FIG. 5.
Figure 7:
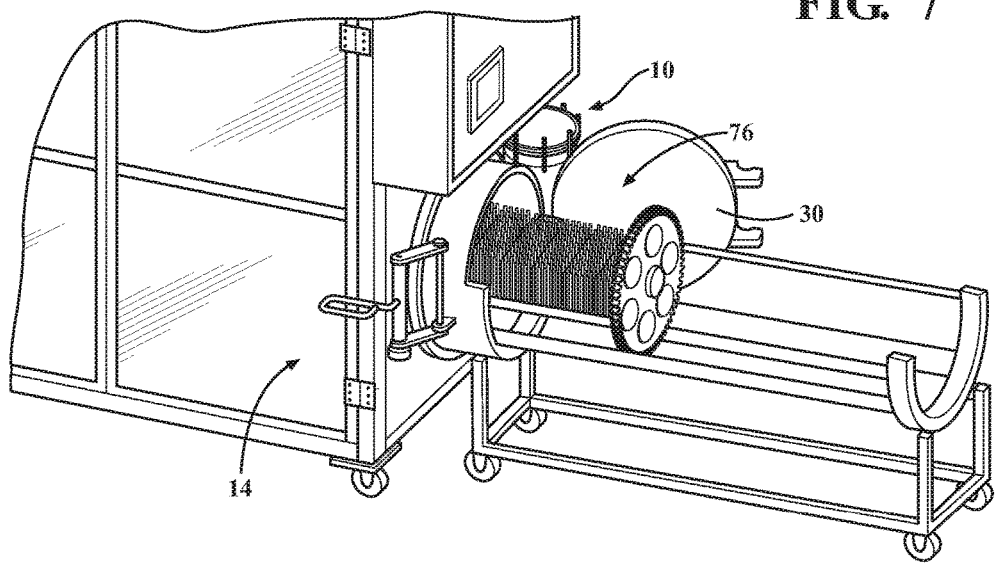
FIG. 7 is a perspective view of a portion of the cleaning apparatus showing a rotatable device being loaded within a chamber of the vessel.

As shown in FIGS. 3, 5, and 6, the apparatus 10 further comprises a vessel 52 within the interior 18 of the housing 14. The vessel 52 includes at least one wall 54 and defines a chamber 56. In an example, the vessel 52 has a single, continuous wall 54 and is generally cylindrical. Alternatively, the vessel 52 may otherwise have a plurality of walls 54 defining a polygonal-shaped vessel, such as a quadrilateral-shaped vessel, a pentagonal-shaped vessel, a hexagonal-shaped vessel, a heptagonal-shaped vessel, an octagonal-shaped vessel, etc. Additionally, the vessel 52 defines a longitudinal axis $A_V$ extending between the first 58 and second 60 ends of the vessel 52. The vessel 52 may comprise various materials, such as steel, plastic, and other materials that will be resistant to the cleaning fluids and mechanical strain generated during the cleaning processes.

The chamber 56, which is defined by the vessel 52, typically reflects the internal shape of the vessel 52. In the illustrated embodiment, the chamber 56 is cylindrically-shaped. The chamber 56 also extends along the longitudinal axis $A_V$ of the vessel 52. In an example, and as shown, the vessel 52 defines a single (i.e., one) chamber 56. In another example, the vessel 52 defines two or more independent chambers.

The vessel 52 also defines a port 62. Alternatively, the vessel 52 may include a plurality of ports 62. As shown, the port 62 is one of a plurality of ports 62 extending along the vessel 52. In an example, the plurality of ports 62 is positioned in an orientation that is substantially parallel to the longitudinal axis $A_V$ of the vessel 52. However, it should be understood that the ports 62 may be located at various other positions of the vessel 52, and may be arranged in other orientations. For example, several strips of ports 62 may be located around the vessel 52 such that the ports 62 are equidistant from one another in the radial and/or longitudinal dimensions. Some of the ports 62 may be used for at least partially filling the chamber 56 with the cleaning fluid. Other 62 ports may be used for injecting air or water. The ports 62 may be shaped and sized according to the type of fluid being transmitted therethrough.

The apparatus 10 further includes an injector 64 operatively coupled (e.g., mechanically attached) to the vessel 52 and in fluid communication with one or more of the ports 62. As shown, the injector 64 is one of a plurality of injectors 64 with each injector 64 operatively coupled to the vessel 52 and in fluid communication with a respective one of the ports 62. The injector(s) 64 may be coupled to a water source (not shown) by a connector 67 for injecting water retrieved from the water source into the chamber 56 through the port 62 and towards the instrument 12. The water is typically injected into the chamber 56 during a rinsing phase of the cleaning method. Details of the cleaning method are set forth below. Further, the injector(s) 64 typically injects water by spraying the water into the chamber 56. In an example, the injector(s) 64 injects the water into the chamber 56 at a flow rate of, for example, from 0.1 to 20 gallons per minute (gpm). In an example, the water sprayed into the chamber 56 by the injector(s) 64 may be pressurized. The pressurized water may effectively remove the cleaning fluid from the exterior and/or interior the instrument during the rinsing step of the cleaning method. Additionally, the water which is sprayed during the rinsing phase may be solely water, and typically does not include any chemical-based cleaning fluids, soaps, detergents, or antimicrobial compounds.

In an example, one or more of the injector(s) 64 may be coupled (such as mechanically attached) to an air source (not shown) a connector 67 for injecting air retrieved from the air source into the chamber 56. The air may be injected through one or more of the ports 62 and towards the instrument 12. It is to be understood that the ports 62 for injecting air into the chamber 56 may different from the ports 62 for filling the chamber 56 with the cleaning fluid. The air that is injected into the chamber 56 maybe at room temperature (such as from 20 to 25° C.) or may be heated. The heated air may have a temperature of from 35 to 45° C. The air may be injected into the chamber 56 during a cleaning phase to heat the cleaning fluid at least partially filling the chamber 56. The air may also or otherwise be injected into the chamber 56 during a drying phase of the cleaning method to partially or completely dry the instrument 12 after the instrument 12 has gone through a cleaning phase of the cleaning method. In an example, the air may be heated utilizing an inline electrical resistance heater (not shown) with a spiral wound open coil heating element. The heater is typically located upstream of the port 62 defined in the vessel 52 which is in fluid communication with the injector 64.

In an example, the apparatus 10 further comprises a valve 66 operatively coupled (such as mechanically attached) to the vessel 52 for controlling flow of the cleaning fluid into the chamber 56 through the one or more ports 62. As shown, the valve 66 is one of a plurality of valves 66 operatively coupled to the vessel 52. The valve 66 may be positioned such that the valves are parallel to the longitudinal axis $A_V$ of the vessel 56. It should be understood that the one or more valves 66 may also be positioned in various orientations relative to the vessel 52. The valve(s) 66 is operatively coupled to a cleaning fluid, and controls the passage of the cleaning fluid from the cleaning fluid source through a pipe, a tube, a conduit, a duct, a channel, and/or the like (not shown), and into the chamber 56. Typically, the valve(s) 66 is coupled to the pipe, tube, conduit, duct, channel, and/or the like utilizing a connector 67. In an example, when the valve(s) 66 is opened, the cleaning fluid flows into the chamber 56 and at least partially fills the chamber 56 with the cleaning fluid. It is to be understood that the valve(s) 66 may allow flow of the cleaning fluid in one direction, such as from the cleaning fluid source to the chamber 56. In an example, the apparatus 10 may further include a drain valve 68 to drain the cleaning fluid from the chamber 56 of the vessel 52.

The valve(s) 66 may include multi-turn valve configurations or quarter-turn valve configurations. Multi-turn valves typically have a closure member that is displaced linearly by turning a stem multiple times. Some non-limiting embodiments of multi-turn valves include gate valves, needle valves, and pinch valves. Quarter-turn valves typically have a closure member that turns 0° to 90° between a fully open position and a fully closed position. Some non-limiting embodiments of quarter-turn valves include ball valves, butterfly valves, plug valves, and spherical valves.

As previously mentioned, the valve(s) 66 may be opened to introduce the cleaning fluid into the chamber 56. This typically occurs during the cleaning phase of the cleaning method. Additionally, the valve(s) 66 may be used to control the flow rate of the cleaning fluid as the cleaning fluid is introduced into the chamber 56. In an example, the valve(s) 66 introduce the cleaning fluid into the chamber 56 at any desirable flow rate. Further, the flow rate of the cleaning fluid can vary or remain constant as the chamber 56 is being at least partially filled.

In an example, the apparatus 10 further comprises an ultrasonic transducer 70 operatively coupled (such as mechanically attached) to the vessel 52 for delivering ultrasonic energy to the cleaning fluid in the chamber 56. As shown, the ultrasonic transducer 70 is one of a plurality of ultrasonic transducers 70 operatively coupled to the vessel 52. The plurality of ultrasonic transducers 70 may be aligned parallel to the longitudinal axis $A_V$ of the vessel 52. Alternatively, the ultrasonic transducers 70 may be positioned in alternative arrangements relative to the vessel 52. For example, the ultrasonic transducers may be positioned in an equidistant manner along the circumference around the vessel 52 and/or parallel to the longitudinal axis $A_V$ of the vessel 52.

The ultrasonic transducer(s) 70 are used for delivering ultrasonic energy to the cleaning fluid inside the chamber 56 of the vessel 52. The ultrasonic transducers 70 can also be described as sonication devices for applying sound energy to the cleaning fluid that is disposed within the chamber 56 to sonicate (e.g. induce fluid cavitation by delivering ultrasonic energy to) the cleaning fluid inside the chamber 56. In certain embodiments, to work properly, the ultrasonic transducers 70 directly contact the cleaning fluid inside the chamber 56. As such, the ultrasonic transducers 70 may be arranged in a manner so that they contact cleaning fluid when the chamber is at least 50, 60, 70, 80, or 90% filled with the cleaning fluid.

Each ultrasonic transducer 70 may operate at a power output of from 0.5 to 1.5 kilowatts (kW). In another example, each ultrasonic transducer 70 may operate at a power output of from 0.75 kW to 1.25 kW. In one particular example, each ultrasonic transducer 70 may operate at a power output of about 1 kW. Additionally, when a plurality of ultrasonic transducers 70 are present, the ultrasonic transducers 70 collectively have, for example, a power output of from 0.1 to 10 kW. In another example, the ultrasonic transducers 70 collectively operate at a power output of from 1 kW to 9 kW. Furthermore, the ultrasonic transducer(s) 70 apply ultrasonic energy to the cleaning fluid inside the chamber 56 at an ultrasonic frequency of from 40 to 140 kilohertz (kHz). In another example, the ultrasonic transducer(s) 70 apply ultrasonic energy to the cleaning fluid inside the chamber 56 at an ultrasonic frequency of from 120 to 140 kHz. In still another embodiment, the ultrasonic transducers 70 apply ultrasonic energy to the cleaning fluid inside the chamber 56 at an ultrasonic frequency of about 132 kHz.

The inventors surprisingly discovered that sonication of the cleaning fluid inside the chamber 56 at the aforementioned ultrasonic frequency ranges effectively removes or breaks up particles of debris, dirt, biological fluids, contaminants, and/or the like from both the interior and exterior surfaces of the instrument 12.

In an example, the apparatus 10 may include a controller 72 in selective communication with each of the ultrasonic transducers 70. The controller 72 is configured to control the power output and frequency of each of the ultrasonic transducers 70. For example, the controller 72 may independently control the frequency and power of each ultrasonic transducer 70, or the controller 72 may control the frequency and power of multiple ultrasonic transducers 70 at once. The controller 72 is or includes a processing unit having a non-transitory, computer-readable storage medium with one or more executable programs stored thereon. One of the executable programs includes computer-readable instructions for automatically setting each ultrasonic transducer 70 to a particular power and/or frequency output. In an example, the program includes computer-readable instructions for setting all of the ultrasonic transducers 70 to one particular power output. In another example, the program includes computer-readable instructions for setting each of the ultrasonic transducers 70 to a different power output. The controller 72 may also be used for monitoring the ultrasonic energy delivered by each of the ultrasonic transducers 70. For example, the controller 72 includes another executable program including computer-readable instructions for measuring the amount of ultrasonic energy (i.e., the power output) by determining a percentage of the ultrasonic energy being delivered by each of the ultrasonic transducers 70. The amount of ultrasonic energy may be used by the controller 72, for example, for making adjustments to the power output of one or more of the ultrasonic transducers 70.

In an example, the apparatus 10 further includes a vacuum pump 74 operatively coupled (such as mechanically attached, such as through pipes, conduits, etc. or fastened directly to and in fluid communication directly with the vessel 52) to the vessel 52 for depressurizing the chamber 56 of the vessel 52. Said differently, the vacuum pump 74 is used for creating at least a partial vacuum in the chamber 56. Depressurization of the chamber 56 involves removing air from within the chamber 56. Depressurization of the chamber 56 also involves removing air bubbles from the cleaning fluid inside the chamber 56 of the vessel 52. The removal of air/air bubbles from the cleaning fluid ensures that molecules of the cleaning fluid, rather than molecules of air, directly contact and/or clean the debris, dirt, biological fluid, etc. on the surface(s) of the instrument 12. In other words, the depressurization of the chamber 56 ensures that air does not interfere with the action of the vibrating cleaning fluid. In an example, the vacuum pump 74 depressurizes the chamber 56 to achieve a maximum vacuum level inside the chamber 56 of about 25 inches of Hg. In an example, the pressure of the chamber 56 when depressurized ranges from atmospheric pressure (which is about 29.9 inches of Hg) to 25 inches of Hg.

Referring to FIGS. 1 and 7-11, the apparatus 10 further includes the rotatable device 76, which is removably disposable in the chamber 56 of the vessel 52. The rotatable device 76 is used for supporting, holding, and/or retaining the instrument(s) 12 during a cleaning process or method. The rotatable device 76 defines a longitudinal axis $A_R$, and the rotatable device 76 is rotatable about the longitudinal axis $A_R$. As shown, the rotatable device 76 has a base 78 having at least one support member 80 with first 82 and second 84 end members coupled (such as mechanically, metallurgically, and/or chemically attached) to the support member 80. In an example, the support member 80 includes a plurality of hollow beams 81 that form a grid. However, it should be appreciated that the rotatable device 76 may have different structures so long as the rotatable device 76 can rotate within the chamber 56 of the vessel 52.

Figure 11:
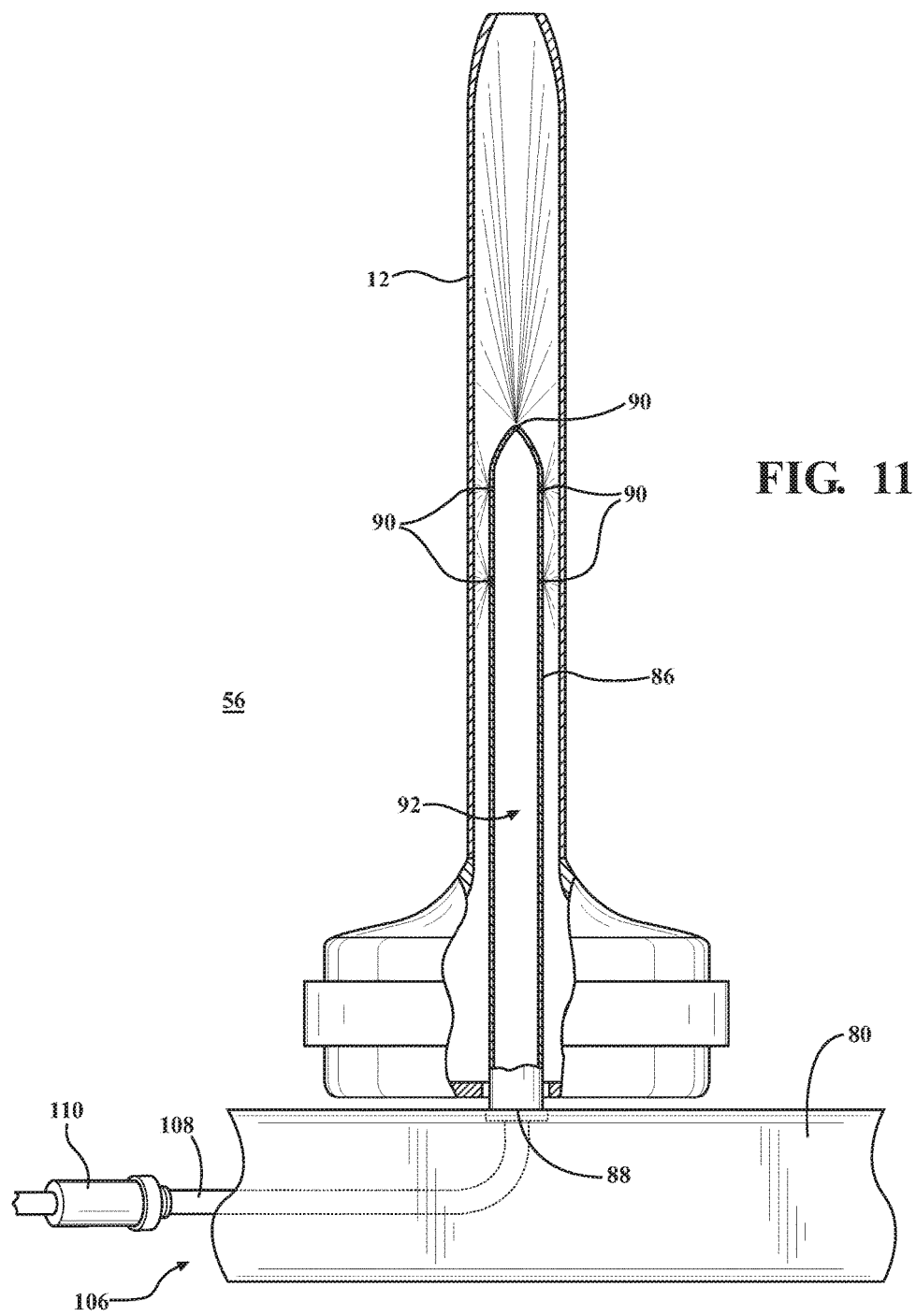
FIG. 11 is a cross-sectional view of a portion of the rack showing a fluid delivery member.

The rotatable device 76 may include a fluid delivery member 86. The fluid delivery member 86 may be oriented transverse to the longitudinal axis $A_R$ of the rotatable device 76. In other words, the fluid delivery member 86 may be oriented such that the fluid delivery member 86 extends away from the rotational axis of the rotatable device 76. As shown, the fluid delivery member 86 is one of a plurality of fluid delivery members 86. The fluid delivery member 86 may be a pin, a stem, a projection, or any suitable structure capable of delivering fluid. As shown in FIG. 11, for example, the fluid delivery member 86 has an inlet 88 and an outlet 90 and defines a fluid channel 92 extending between the inlet 88 and the outlet 90. In an example, the outlet 90 is defined at the tip of the fluid delivery member 86. In another example, the outlet 90 is defined at the side of the fluid delivery member 86. In still another example, the outlet 90 is defined at a distal end of the fluid delivery member 86. In still another example, the fluid delivery member 86 may have a plurality of outlets 90 with one outlet 90 defined at the tip of the fluid delivery member 86 and one or more outlets 90 defined at the side of the fluid delivery member 86. The inlet 88 may be defined at the bottom of the fluid delivery member 86 as shown. The fluid delivery member(s) 86 may be dimensioned in various manners such that they are capable of delivering cleaning fluid to the interior of the instruments being cleaned.

As will be described in further detail below, the cleaning fluid is circulated utilizing a fluid transmission system 106 from the chamber 56 and through the fluid channel 92 of the fluid delivery members 86 during the cleaning phase of the cleaning method.

In an example, the rotatable device 76 further includes a wheel 94 coupled (such as mechanically, metallurgically, and/or chemically attached) to the base 78. More specifically, the wheel 94 is coupled to one of the first 82 or second 84 end members of the base 78. As shown, the wheel 94 is coupled to the end member 82 of the base 78. In an example, the wheel 94 includes a plurality of teeth 96 that interlocks with teeth of a gear (not shown) disposed on the vessel 52. Typically, the gear rotates in response to a rotational force applied to the gear from, e.g., a motor or some other power source (not shown), to rotate the wheel 94 which causes the rotatable device 76 (which includes the wheel 94) to rotate as well. While the rotatable device 76 is shown including a single (i.e., one) wheel 94, it is to be understood that the rotatable device 76 may include a wheel 94 coupled to both end members 82, 84 of the rotatable device 76. In this case, the two gears would be coupled to the vessel 52 for interlocking with the teeth 96 of the wheels 94 and rotate the rotatable device 76.

The rotatable device 76 further includes a rack 98 defining a cavity 100 for supporting the instrument 12. The rack 98 is attachable to the rotatable device 76, such as to the support member 80. The rack 98 may also extend parallel to the longitudinal axis $A_R$ of the rotatable device 76. In an example, the rotatable device 76 includes a single (i.e., one) rack 98, which extends along the length of the rotatable device 76 and parallel to the longitudinal axis $A_R$. In another example, and as shown, the rotatable device 76 includes a plurality of racks 98 which are aligned and/or are adjacent to one another and each extends along a portion of the length of the rotatable device 76.

Figure 8:
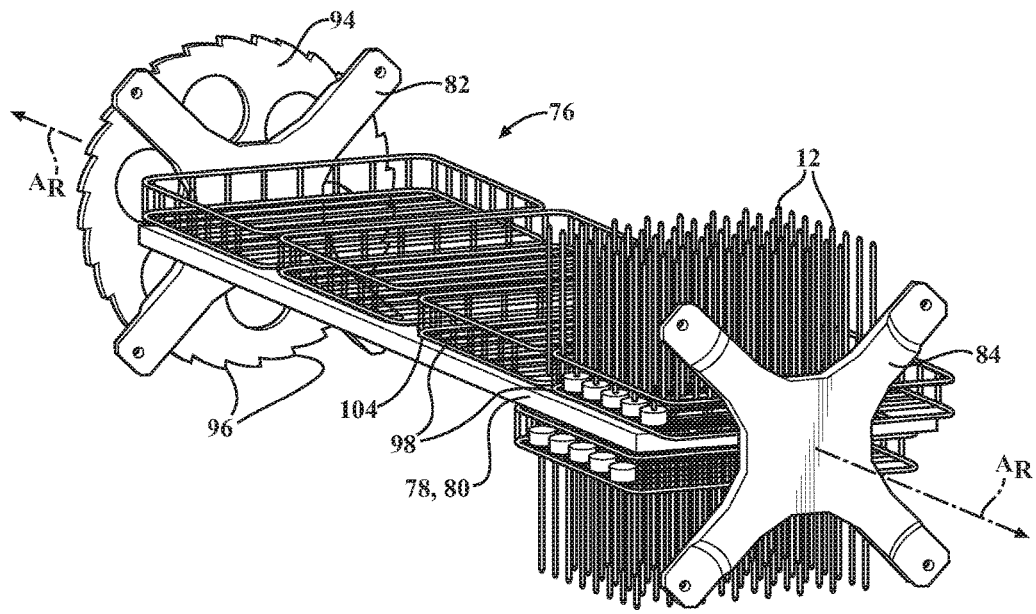
FIG. 8 is a perspective view of an embodiment of the rotatable device for the cleaning apparatus.
Figure 9:
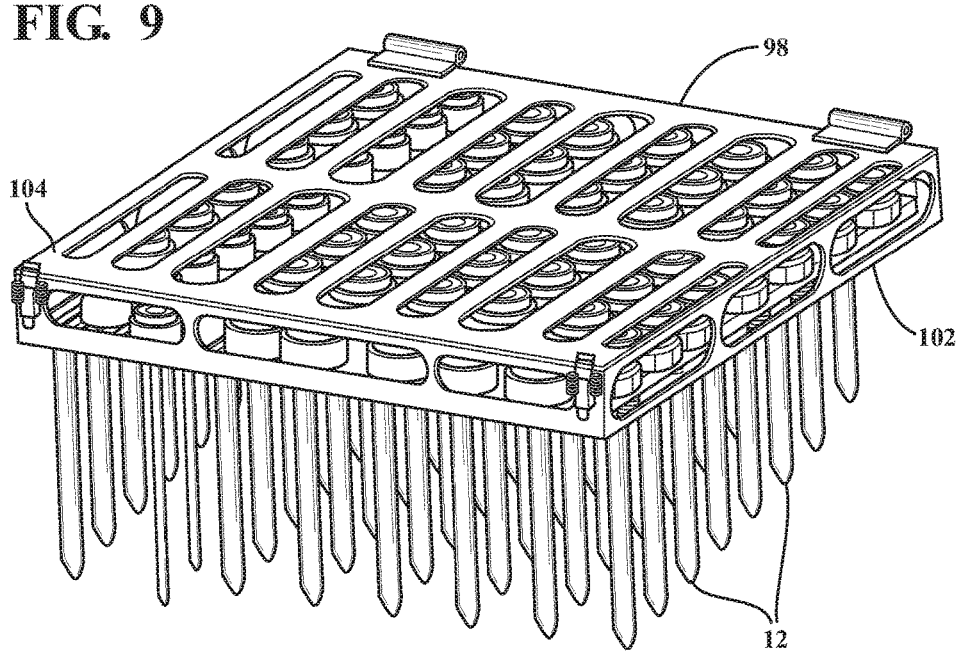
FIG. 9 is a perspective view of an embodiment of a rack for the rotatable device where the rack defines a cavity with an instrument supported in the cavity.
Figure 10:
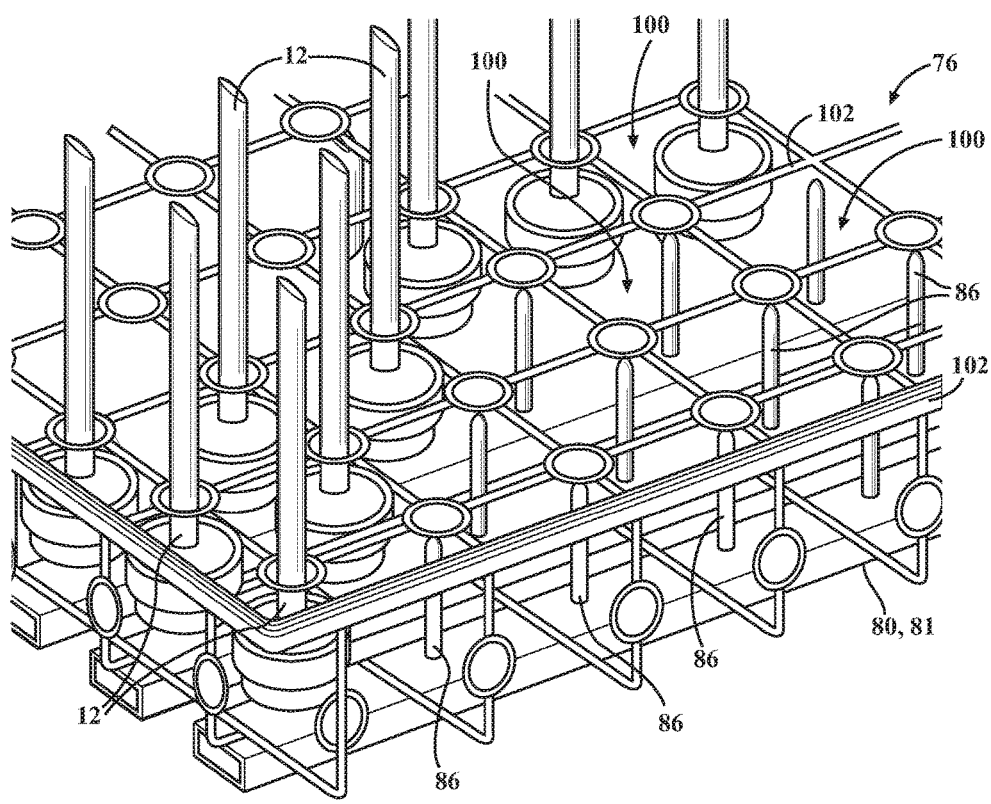
FIG. 10 is a cut-away view of a portion of the rack with instruments disposed therein.

In an example, and as shown in FIG. 8, the rack(s) 98 has a top 102 and bottom 104 portions with each portion 102, 104 having a plurality of rods defining a grid-like structure. In an example, each rack 98 defines a plurality of cavities 100 between the top 102 and bottom 104 portions with a fluid delivery member 86 extending towards each of the cavities 100. However, it should be appreciated that the rack 98 may have other configurations so long as the rack 98 is capable of securing the instrument(s) 12 during the cleaning method or process. An example of another configuration of the rack 98 is shown in FIG. 9. In this example, the top and bottom portions 102, 104 have slots rather than a grid-like structure. Additionally, the bottom portion 104 is at least partially removable from the top portion 102 for loading of the instrument(s) 12 in the rack 98, and the bottom portion 104 is attachable to the top portion 102 (e.g., after the instrument(s) 12 has been loaded) utilizing fasteners, buckles, clasps, etc.

Typically, each fluid delivery member 86 aligns with a respective instrument 12 to be cleaned. In certain embodiments, the fluid delivery member 86 may be placed within (or at least partially within) the interior and/or the lumen of the instrument 12 as the instrument 12 is loaded into the rack 98. In one example, the fluid delivery member 86 may also hold, support, and/or retain the instrument 12. In another example, the instrument 12 may be held, supported, and/or retained by the top and bottom portions 102, 104 of the rack 98. In an example, the top portion 102 of the rack 98 may be vertically adjusted to accommodate for any type, shape, and/or design of the instrument 12. Further, when cleaning a plurality of instruments 12, the top portion 102 may have apertures each defining a portion of a cavity 100 at each instrument location, where the narrowest portion of the instrument 12 is allowed to pass through the top portion 100 while the widest portion of the instrument 12 remains inside the cavity 100 and acts as a shoulder. This configuration typically prevents undesirable movement and/or passage of the instrument 12 through the rack 98 during the cleaning method.

It is to be understood that the instrument 12 is loosely (i.e., not rigidly) held, supported, and/or retained by the fluid delivery member 86 and/or the rack 98 so that the instrument 12 does not get damaged (e.g. broken, cracked, scraped, etc.) during the cleaning method. Further, by virtue of being loosely held, supported, and/or retained by the fluid delivery member 86 and/or the rack 98, the instrument 12 can oscillate slightly while the rotatable device 76 rotates and/or while the ultrasonic transducers 70 sonicate the cleaning fluid. For example, oscillation of the instrument 12 occurs due, at least in part, to the rotational motion of the rotatable device 76 while submerged in the cleaning fluid inside the chamber 56 during the cleaning method. Additionally, the fluid delivery member 86 and the cavity 100 of the rack 98 are designed so there is/are dimensional clearance(s) between the fluid delivery member 86 and the instrument 12.

In instances where the instrument 12 does not call for internal cleaning, the rotatable device 76 may not include a fluid delivery member 86. In this instance, the top portion 102 of the rack 98 may be sufficient to prevent undesirable movement of the instrument 12 within the rack 98.

As previously mentioned, the apparatus 10 may further include a fluid transmission system 106. The fluid transmission system 106 may be in fluid communication with the chamber 56 and the fluid channel 92 of the fluid delivery member 86 for circulating the cleaning fluid from the chamber 56 through the fluid channel 92 of the fluid delivery member 86. In the example shown in FIG. 11, the fluid transmission system 106 has a conduit 108 in fluid communication with the chamber 56 and a pump 110 operatively coupled (such as mechanically attached) to the conduit 108 for circulating the cleaning fluid from the chamber 56 through the fluid channel 92 of the fluid delivery member 86. For example, the instrument 12 is submerged in the cleaning fluid which at least partially fills the chamber 56. When submerged, the cleaning fluid contacts the exterior of the instrument 12 as well as the interior of the instrument 12. The cleaning fluid is retrieved from the chamber 56, and is transported through the conduit 108 and into the fluid channel 92 of the fluid delivery member 86. The fluid flows through the fluid channel 92 and through the outlet(s) 90 defined in the fluid delivery member 86. Based, at least in part, on the flow rate of the cleaning fluid flowing through the conduit 106 and the fluid channel 92, the cleaning fluid jets out of the outlet(s) 90 of the fluid delivery member 86 and contacts the interior surface(s) and/or lumen of the instrument 12. Additionally, since the instrument 12 is submerged in the cleaning fluid in the chamber 56, the interior of the instrument 12 is already filled with cleaning fluid. Accordingly, the cleaning fluid that is jetted from the fluid delivery member 86 contacts the cleaning fluid already present inside the instrument 12. Said differently, the jetting of the cleaning fluid from the fluid delivery member 86 occurs at or through a liquid-to-liquid interface. Accordingly, when jetted, the cleaning fluid does not contact air. It is to be understood that the design of the fluid delivery member 86 is specific for achieving the desirable jetting of the cleaning fluid into the interior of the instrument 12 that occurs at or through a liquid-to-liquid interface. It is further to be understood that the jetting of the cleaning fluid into the interior of the instrument 12 cannot be accomplished by a nozzle (i.e., a device that utilizes a spray or atomization of a liquid through air (e.g. via an air interface) under pressure.

In the example depicted in FIG. 11, the conduit 108 extends through the hollow beams 81 of the support member 80. Alternatively, the support member 80 may be solid and bottom portion of the rack 98 may be hollow. In this case, the conduit 108 may extend through the bottom portion 104 of the rack 98 and is in fluid communication with the inlet 88 of the fluid delivery member 86. Also in this case, the bottom portion 104 of the rack 98 may be attached to the support 80 and the top portion 102 may be removable for loading the instrument(s) 12.

In an example, the apparatus 10 further includes a receptacle 112 for holding the cleaning fluid. A conduit 114 is in fluid communication with the receptacle 112 and with the port 62 of the vessel 52 for at least partially filling the chamber 56 with the cleaning fluid. The conduit 114 further has a valve (such as the valve 66) for controlling flow of the cleaning fluid from the receptacle to the chamber 56. In an example, the apparatus 10 has a plurality of receptacles 112 each for holding a different cleaning fluid, and a has a plurality of conduits 114 and an associated pump 116 with each conduit 114 in fluid communication with a respective one of the receptacles 112.

In an example, the pump 116 is a positive displacement pump. Some non-limiting embodiments of positive displacement pumps include rotary pumps, diaphragm pumps, piston displacement pumps, gear pumps, and the like. Typically, the pump 116 pulls the cleaning fluid from the receptacle 112 and the valve 116 controls the flow rate of the cleaning fluid into the chamber 56. In an example, the cleaning fluid enters the chamber 56 at a flow rate of up to about 44 gallons per minute (gpm). However, other flow rates are also contemplated depending on the scale of the apparatus.

In an example, and as shown in FIGS. 2 and 3, the pump(s) 116 may be situated adjacent to or inside the housing 14. In another example, the pump(s) 116 may be situated on a tray 118 that is moveable between open and closed positions. An example of the open position of the tray 118 is shown in FIG. 3, while an example of the closed position of the tray 118 is shown in FIG. 2. The tray 118 may be received inside the housing 14 through, e.g., an aperture 120 formed in the front wall 16$_C$ of the housing 14. As shown, the tray 118 includes a base 122 that supports the pump(s) 116 and a side panel 124. Opposing sides of the base 122 may be received in tracks (not shown) formed in the frame 20 of the housing 14, allowing the base 122 to be moveable relative to the housing 14 along the tracks. When the tray 118 is in the closed position, the base 122 of the tray 118 may be completely received in the housing 14, and the side panel 124 covers the aperture 120 and forms part of the front wall 16$_C$.

In an example, the cleaning apparatus 10 further includes a processor 126 for operating the apparatus 10 according to a predetermined cleaning protocol. The processor 126 may be a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing functions associated with the apparatus 10. The processor 126 has a non-transitory, computer-readable storage medium with a plurality of executable programs stored thereon. Each of the executable programs contains computer-readable instructions for a respective, predetermined cleaning protocol. The cleaning protocol typically includes one or more steps for cleaning the instrument 12. The steps may include, but are not limited to, a high power rinse step, a chamber filling step, a washing step, a draining step, and a drying step. The cleaning protocol also includes various parameters that are used during the cleaning, such as flow rates of the cleaning fluid, rinse water, and/or air, pressure inside the chamber 56, power output of the ultrasonic transducers 70, duration (in terms of seconds, minutes, hours, etc.) for each step, fluid and/or air temperature, etc.

The cleaning protocols may be created by a user of the apparatus 10, such as an operator and/or an engineer of the apparatus 10. The cleaning protocol can be saved or stored as one of a plurality of cleaning protocols, and all of the cleaning protocols remain resident on the processor 126 of the apparatus 10. Alternatively, the cleaning protocol(s) may be customized ad hoc such that users of the instruments can create new protocols. Further, the apparatus 10 includes a user interface 128 (such as a display screen with a keyboard and mouse, a touch screen, and/or the like), which is operatively associated with the processor 124, for selecting a particular cleaning protocol from the plurality of cleaning protocols resident on the processor 124.

Additionally, and in an example, the processor 124 may be used to control and/or activate various incidental components/aspects of the apparatus 10. For instance, the processor 124 may be used for activating the motor 46 coupled to the front door 30 for opening and closing the front door 30. For instance, the processor 124 may also be used for activating a motor coupled to a gear on the vessel 52 for initiating rotation of the rotatable device 76.

Also disclosed herein is a method for cleaning the instrument 12 utilizing the apparatus 10. The method includes loading the instrument 12 in the rotatable device 76; specifically, in the cavity 100 of the rack 98. For example, the top portion 102 of the rack 98 is removed from the bottom portion 104, or visa versa depending on the design or configuration of the rack 98. The instrument 12 may be aligned with the fluid delivery member 86, and the fluid delivery member 86 is placed within, or at least partially within, the interior and/or lumen of the instrument 12. The instrument is placed in the cavity 100 and the top portion 102 of the rack 98 is placed back on the bottom portion 104 with at least a portion of the instrument 12 being supported between the top 102 and bottom 104 portions of the rack 98.

After the instrument 12 is loaded, the method involves placing the rotatable device 76 inside the chamber 56 of the vessel 52. In an example, and as shown in FIGS. 1 and 12A-12D, the rotatable device 76 may be loaded with the assistance of a cart 130. The cart 130, for example, may be any type of a holder for the rotatable device 76 when the rotatable device 76 is outside of the chamber 56 of the vessel 52. In an example, the cart 130 may be supported by wheels so that the cart 130 can be easily moved from one place to another (e.g. for loading the rotatable device 76 at the front end 24 of the housing 14).

As shown in FIGS. 12A-12D, the loading of the rotatable device 76 includes opening the front door 30, for example, by unlatching the locking mechanism 40 and moving the front door 30 from the closed position to the open position. As shown in FIG. 12A, the loading step further includes moving (e.g. sliding) the rotatable device 76 from outside of the chamber 56, through the front door 30, and into the chamber 56. In some examples, the loading step further includes positioning the cart 130 (with the rotatable device 76 disposed on the cart 130) adjacent the first door 30 and then pushing the rotatable device 76 off of the cart 130, through the front door 30, and into the chamber 56 of the vessel 52. Once the rotatable device 76 has been placed inside the chamber 56 of the vessel 52, the method further comprises closing the front door 30 and locking the front door 30 with the locking mechanism 40. It is to be understood that when the front door 30 and the rear door 50 are closed (and locked), an air-tight and liquid-tight seal is formed within the chamber 56.

Before or after the rotatable device 76 has been loaded into the chamber 56 of the vessel 52, the user of the apparatus 10 selects one of the predetermined cleaning protocols stored in the processor 126 utilizing the user interface 128. While the cleaning protocols differ in terms of number and/or sequence of operational steps and various operational parameters, each protocol typically defines a cleaning method having a cleaning phase, a rinsing phase, and a drying phase. The cleaning phase may include a pre-rinsing stage and a cleaning stage. The pre-rinsing stage involves rinsing the instrument 12 prior to applying the cleaning fluid to the instrument 12, and the cleaning stage involves applying the cleaning fluid to the instrument 12. The rinsing step includes rinsing the instrument 12. While the rinsing phase typically occurs after the cleaning step, in some instances, the rinsing step may also occur prior to the cleaning step. The rinsing step may include a first rinsing stage where the exterior of the instrument 12 is rinsed and a second rinsing stage where the interior of the instrument 12 is rinsed. The drying phase includes drying the instrument 12.

During the cleaning phase, the method comprises at least partially filling the chamber 56 with the cleaning fluid to submerge the instrument 12 in the cleaning fluid. The step of at least partially filling the chamber 56 may be accomplished by retrieving the cleaning fluid from the receptacle 112 and controlling flow of the cleaning fluid from the receptacle to the chamber 56 with the valve 66. As previously mentioned, the valve 66 may be opened to introduce the cleaning fluid into the chamber 56 at any desirable flow rate. Typically, the chamber 56 (with the rotatable device 76 inside the chamber 56) is completely filled with the cleaning. However, completely filling the chamber 56 with the cleaning solution is not required so long as the instrument 12 is completely submerged in the cleaning fluid inside the chamber 56. In an example, the cleaning fluid fills at least 75% of the chamber 56 volume. In still another embodiment, the cleaning fluid fills at least 85% of the chamber 56 volume.

The method further includes rotating the rotatable device 76 within the chamber 56. In an example, the rotatable device 76 rotates within the chamber 56 at a rate of from 0.5 to 1.5 rpm. In another example, the rotatable device 76 rotates within the chamber 56 at a rate of from 0.8 to 1.2 rpm. Alternatively still, the rotatable device 76 may rotate within the chamber at a rate of 0.1 to 10 rpm. The rotation of the rotatable device 76 may be initiated by the processor 126 according to the selected cleaning protocol by powering the motor operatively coupled to the vessel 52 which causes the gear coupled to the vessel 52 to rotate.

It is to be understood that while the rotatable device 76 rotates within the chamber 56, at least one of the fluid delivery member 86 and the instrument 12 oscillate within the rack 98. As previously described, by virtue of being loosely held, supported, and/or retained by the fluid delivery member 86 and/or the rack 98, the instrument 12 can oscillate slightly while the rotatable device 76 rotates while the instrument 12 is submerged in the cleaning fluid. Additionally, the fluid delivery member 86 may also oscillate based, at least in part, on how the fluid delivery member 86 is coupled to the rotatable device 76. Oscillatory movement of the instrument 12 and/or the fluid delivery member 86 causes the cleaning fluid to flow against the interior and exterior surfaces of the instrument 12 for removing at least part of the dirt, debris, biological fluids, etc. from the surfaces of the instrument 12.

It is to be understood that the cleaning phase is accomplished, at least in part, when the instrument 12 is submerged in the cleaning fluid that at least partially fills the chamber 56 of the vessel 52. Accordingly, in certain embodiments, the cleaning fluid is not sprayed over the instrument 12 through air during the cleaning phase.

The method further comprises sonicating the cleaning fluid in the chamber with the ultrasonic transducer 70. In an example, the apparatus 10 includes a plurality of ultrasonic transducers 70 and the sonicating step involves sonicating the cleaning fluid with the ultrasonic transducers 70 with a collective power output of, for example, from 0.1 to 10 kW. Additionally, the sonicating step further involves sonicating the cleaning fluid with the ultrasonic transducers 70 at a frequency of, for example, from 40 to 140 kHz. In an example, sonication utilizing a plurality of ultrasonic transducers 70 each having a power output of from 0.1 to 10 kW and delivering ultrasonic energy at a frequency of from 40 to 140 kHz effectively breaks up particles of the biological fluid or other contaminant(s) for easy removal of the biological fluid or other contaminant(s) from the surface(s) of the instrument 12.

In an example, the method further includes depressurizing the chamber 56 during the cleaning phase. Depressurization of the chamber 56 may be accomplished by creating at least a partial vacuum inside the chamber 56 by evacuating the atmosphere in the chamber 56 to a pressure of from 15 to 25 inches of Hg with the vacuum pump 74.

The sonicating and depressurizing steps may occur separately during the cleaning phase. Alternatively, the sonicating and depressurizing steps occur at the same time. For instance, during the cleaning phase, the instrument 12 is cleaned utilizing sonication while depressurizing the chamber 56. In an example, the chamber 56 is depressurized and the sonication occurs in while the chamber 56 is being depressurized. In another example, depressurization of the chamber 56 occurs after sonication has commenced. In both examples, sonication occurs in the presence of the at least partial vacuum. Sonication while pulling the at least partial vacuum may effectively remove biological fluid or other contaminant(s) from both the interior and exterior surfaces of the instrument 12. When the at least partial vacuum is applied simultaneously with sonication, air is removed from the chamber 56 and the interior and/or lumen of the instrument 12 so that molecules of the cleaning fluid can directly contact the interior of the instrument 12. Also, when the at least partial vacuum is applied simultaneously with sonication, air is removed from the chamber 56 and from the cleaning solution so that molecules of the cleaning solution can directly contact the exterior of the instrument 12.

In an example, the heat may also be applied to the chamber 56 during the sonicating and depressurizing. In an example, heat may be applied by injecting heated air into the chamber 56 utilizing the injector(s) 64. In another example, heat may be applied by pre-heating the cleaning fluid prior to introducing the cleaning fluid into the chamber 56. The air and/or cleaning fluid may be heated using a suitable heating device.

In an example, the rotatable device 76 is rotated continuously, at the prescribed rate in rpm, during the sonicating and depressurizing steps. In another example, the rotatable device 76 is intermittently rotated during the sonicating and depressurizing steps. In the later example, the rotatable device 76 may be rotated periodically (such as every 10 seconds, every 30 seconds, etc.). In still another example, the rotatable device 76 is not rotated at all during the sonicating and depressurizing steps.

During the cleaning phase, the method further comprises circulating the cleaning fluid through the fluid channel 92 of the fluid delivery member 86 such that the cleaning fluid exits the fluid delivery member 86 to contact the interior of the instrument 12. In an example, the fluid transmission system 106 retrieves the cleaning fluid from inside the chamber 56 and circulates the cleaning fluid through the fluid channel 92 of the fluid delivery member 86. For example, the cleaning fluid enters the inlet 88 of the fluid delivery member 86, flows through the fluid channel 92, and exits the fluid delivery member 86 through the outlet 90. It is to be understood that when the cleaning fluid exits the fluid channel 92 through the outlet 90, the cleaning fluid contacts cleaning fluid already inside the interior of the instrument 12. Accordingly, the cleaning fluid exiting the fluid delivery member 86 enters liquid inside the instrument 12; and not air. In an example, the circulating step occurs separately from, or simultaneously with the sonicating and/or depressurizing steps.

After the cleaning phase is complete, in an example, the cleaning method enters the rinsing phase which includes injecting a rinse water into the chamber 56 through the at least one port 62 towards the instrument 12. In an example, the rinse water is injected (e.g. via spraying), under pressure, inside the chamber 56 utilizing the injector 64. Typically, the rinse water is injected while the rotatable device 76 is rotating inside the chamber 56. The rinse water contacts the rotatable device 76, and contacts the instrument 12 retained by the rotatable device 76, to remove any debris from the instrument 12. The rinse water along with the debris may be drained from the chamber 56 via, e.g., the drain valve 68 which may be located at the lowest point of the vessel 52. Water may be drained using the drain valve 68 that can be manually operated or automatically operated by the processor 126.

As previously mentioned, the rinsing phase of the cleaning method may include first and second rinsing stages. During the first rinsing stage, the method comprises rinsing the exterior surface(s) of the instrument 12 with a rinse water to remove additional debris and cleaning fluid from the exterior surface(s) of the instrument 12. In an example, the method comprises rotating the rotatable device 76 further (e.g. at a rate of from 0.5 to 1.5 rpm) while simultaneously introducing (e.g. spraying) a rinse water, under pressure, into the chamber 56 via the injector 64. The rinse water is typically used to rinse off the exterior surface(s) of the instrument 12 that was just in contact with the cleaning fluid during the previous cleaning phase.

It is to be understood that the cleaning phase and first rinsing stage described above may be applied once to the instrument 12, or may be applied several (e.g. two or more) times. The number of cleaning phases and first rinsing stages that are applied may be controlled by the processor 124 according to the selected cleaning protocol.

In an embodiment, the method further includes the second rinsing stage. During the second rinsing stage, the method comprises rinsing the interior surface(s) of the instrument 12 with a rinse water to remove additional debris and cleaning fluid from the interior of the instrument 12. In an example, the method comprises retrieving the rinse water from a rinse water supply, passing the rinse water through the fluid transmission system 106 and into the fluid channel 92 of the fluid delivery member 86. The rinse water exits the fluid delivery member 86 through the outlet 90 and into the interior of the instrument 12. The method further comprises draining the rinse water from the chamber 56, such as with the drain valve 68. The second rinsing stage may be accomplished separately from the first rinsing stage, or simultaneously with the first rinsing stage.

After rinsing the exterior and interior surfaces of the instrument 12, the method further comprises rotating the rotatable device 76 (again at a rate of from 0.5 to 1.5 rpm) while evacuating the atmosphere in the chamber 56. This may be accomplished utilizing the vacuum pump 74. Additionally, and during a drying phase of the cleaning method, the method involves introducing heated air into the chamber 56 to dry the instrument 12. In an example, the heated air used for drying has a temperature of from 40 to 50° C., and drying utilizing the heated air may be accomplished using, e.g. a 10 minute drying cycle time.

When the drying phase is complete, the method further comprises unlocking the rear door 50 and moving the rear door 50 to an open position. The method comprises moving the rotatable device 76 (e.g. via sliding) out of the chamber 56 through the rear door 50. The method further comprises removing the instrument 12 from the rotatable device 76.

A specific embodiment of a cleaning protocol is set forth below:

1. Sliding the rotatable device 76 from an interior of the chamber 56 to an exterior of the chamber 56 for loading;
2. Loading the one or more instruments 12 (such as trocars) into respective cavities 100 of the rack 98, where the instruments 12 are lined up with a respective one of the fluid delivery members 86;
3. Sliding the loaded rotatable device 76 from the exterior of the chamber 56 to the interior of the chamber 56 for cleaning;
4. Locking the front 30 and rear 50 doors;
5. Rotating the rotatable device 76 at approximately 1 rpm while simultaneously spraying a rinse water, under pressure, through the injectors 64 to contact the instruments 12 and remove large debris from the instruments 12;
6. Draining the chamber 56 of the rinse water and the large debris;
7. Filling the chamber 56 with a cleaning fluid such that the chamber 56 fills from the bottom to the top of the chamber 56;
8. Sonicating the cleaning fluid in the chamber 56 at a frequency of about 132 kHz utilizing the ultrasonic transducers 70;
9. Evacuating an atmosphere in the chamber 56 to approximately 20 inches of Hg utilizing the vacuum pump 74;
10. Transmitting the cleaning solution through the fluid transmission system 106 into the interior of the instruments 12 simultaneously with, or independently from, steps 7, 8, and/or 9;
11. Optionally rotating the rotatable device 76 simultaneously with steps 7, 8, 9, and/or 10;
12. Draining the chamber 56 of the cleaning fluid;
13. Rotating the rotatable device 76 at approximately 1 rpm while simultaneously spraying a rinse water, under pressure, to contact the instruments 12;
14. Repeating steps 7, 8, 9, 10, 11, and 12;
15. Filling the chamber 56 with rinse water utilizing the injectors 64;
16. Repeating steps 8, 9, and 10;
17. Transmitting the rinse water through the fluid transmission system 106 into the interior of the instruments 12 simultaneously with, or independently from, any one or more parts of step 16;
18. Draining the chamber 56 of the rinse water;
19. Repeating step 13;
20. Rotating the rotatable device 76 at approximately 1 rpm while simultaneously evacuating the atmosphere in the chamber 56 utilizing the vacuum pump 74 and injecting heated air through the injectors 64 to dry the instruments 12;
21. Unlocking and opening the rear door 50; and
22. Removing the rotatable device 76 from the chamber 56 and removing the instruments 12 from the rotatable device 76.

The apparatus 10 and method described above may be used to efficiently and effectively clean both the interior and the exterior of instruments, such as medical instruments. The apparatus 10 utilizes cleaning protocols to perform the cleaning method with process controls so that the instruments 12 may be cleaned within acceptable cleaning standards. Yet further, the apparatus requires less handling of the instruments 12 during cleaning, which reduces breakages or damage to the instruments 12 as well as the individual components of the apparatus 10.

While the invention has been described with reference to the examples above, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all examples falling within the scope of the appended claims.

What is claimed is:

1. A method for cleaning an instrument with a cleaning fluid, said method comprising the steps of:
   providing the instrument, wherein the instrument comprises a lumen;

providing a vessel defining a chamber;
providing a rack defining a cavity and a projection extending towards the cavity with the projection having a length, an inlet, an outlet, and a fluid channel extending along the length between the inlet and the outlet;
providing a rotatable device defining a longitudinal axis, wherein the rotatable device comprises the rack such that the rack can be rotated;
loading the instrument in the cavity defined by the rack such that the projection extends at least partially within the lumen of the instrument;
disposing the rack with the loaded instrument inside the chamber of the vessel;
at least partially filling the chamber with the cleaning fluid to submerge the instrument in the cleaning fluid;
sonicating the cleaning fluid in the chamber with an ultrasonic transducer;
rotating the rotatable device including the rack about the longitudinal axis within the chamber while the projection extends at least partially within the lumen of the instrument; and
circulating the cleaning fluid through the fluid channel of the projection such that the cleaning fluid exits the projection through the outlet and contacts the lumen of the instrument, wherein the circulating step is performed while the projection extends at least partially within the lumen and while the rack and instrument remain within the chamber.

2. The method as set forth in claim 1 wherein the sonicating step is further defined as sonicating the cleaning fluid with the ultrasonic transducer at a frequency of from 40 to 140 kHz.

3. The method as set forth in claim 1 wherein the ultrasonic transducer of the apparatus is one of a plurality of ultrasonic transducers and the sonicating step is further defined as sonicating the cleaning fluid with the plurality of ultrasonic transducers collectively having a power output of from 0.1 to 10 kW.

4. The method as set forth in claim 1 wherein the vessel further defines a port and further comprising the step of injecting a rinse water into the chamber through the port.

5. The method as set forth in claim 1 wherein the vessel further defines a port and further comprising the step of injecting air into the chamber through the port.

6. The method as set forth in claim 5 further comprising the step of heating the air prior to injecting the air into the chamber.

7. The method as set forth in claim 1 further comprising the step of depressurizing the chamber.

8. The method as set forth in claim 7 wherein the depressurizing step occurs simultaneously with the sonicating step.

9. The method as set forth in claim 1 further comprising the steps of:
providing a receptacle for holding the cleaning fluid and a conduit in fluid communication with the receptacle and the chamber with the conduit having a valve;
retrieving the cleaning fluid from the receptacle; and
controlling flow of the cleaning fluid from the receptacle to the chamber with the valve.

10. The method as set forth in claim 1 wherein the rack has a top and a bottom with the cavity defined between the top and the bottom and said loading step further includes:
placing the projection at least partially within the lumen of the instrument; and
placing the instrument in the cavity with at least a portion of the instrument supported between the top and bottom of the rack.

11. The method as set forth in claim 10 further comprising the step of:
oscillating at least one of the projection and the instrument during the rotating step.

12. The method as set forth in claim 1 wherein the circulating step further includes jetting the cleaning fluid from the outlet of the projection into the lumen of the instrument while the instrument is submerged in the cleaning fluid.

13. A method for cleaning an instrument with a cleaning fluid, said method comprising the steps of:
providing the instrument, wherein the instrument comprises an interior and an exterior;
providing an apparatus having a vessel defining a chamber and a port, a rack defining a cavity for supporting the instrument, and a fluid delivery member extending towards the cavity and having an inlet, an outlet, and a fluid channel extending between the inlet and the outlet;
loading the instrument in the cavity of the rack such that the fluid delivery member extends into the interior of the instrument when the instrument is loaded in the cavity;
placing the rack inside the chamber of the vessel;
at least partially filling the chamber with the cleaning fluid to submerge the instrument in the cleaning fluid;
sonicating the cleaning fluid in the chamber with an ultrasonic transducer;
rotating the rack about a longitudinal axis within the chamber during the sonicating step while the fluid delivery member extends into the interior of the instrument; and
circulating the cleaning fluid through the fluid channel of the fluid delivery member such that the cleaning fluid exits the fluid delivery member and contacts the interior of the instrument, wherein the circulating step is performed while the fluid delivery member extends into the instrument's interior and while the rack and instrument remain within the chamber.

14. The method as set forth in claim 13 wherein the sonicating step is further defined as sonicating the cleaning fluid with the ultrasonic transducer at a frequency of from 40 to 140 kHz.

15. The method as set forth in claim 13 further comprising the steps of:
providing a rotatable device defining a longitudinal axis with the rotatable device including the rack; and
rotating the rotatable device within the chamber during the sonicating step.

16. The method as set forth in claim 13 further comprising the step of depressurizing the chamber.

17. The method as set forth in claim 13 wherein the apparatus further has a receptacle for holding the cleaning fluid and a conduit in fluid communication with the receptacle and the chamber with the conduit having a valve and said method further comprising the steps of:
retrieving the cleaning fluid from the receptacle; and
controlling flow of the cleaning fluid from the receptacle to the chamber with the valve.

18. The method as set forth in claim 13 wherein the rack has a top and a bottom with the cavity defined between the top and the bottom and said loading step further comprises:
placing the fluid delivery member within the interior of the instrument; and placing the instrument in the cavity with at least a portion of the instrument supported between the top and bottom of the rack.

19. The method as set forth in claim 18 further comprising the steps of:
providing a rotatable device defining a longitudinal axis with the rotatable device including the rack;
rotating the rotatable device within the chamber; and
oscillating at least one of the fluid delivery member and the instrument during the rotating step.

* * * * *